United States Patent [19]
Scotto

[11] Patent Number: 5,386,732
[45] Date of Patent: Feb. 7, 1995

[54] MODULAR SYSTEM OF LOW COST FORM OF CONSTRUCTION FOR APPLICATION-OPTIMIZED FLUENT DENSITY AND MASS FLOW SENSORS

[75] Inventor: Dominick Scotto, Plainview, N.Y.
[73] Assignee: miniMaxinc, Forest Hills, N.Y.
[21] Appl. No.: 89,127
[22] Filed: Jul. 8, 1993
[51] Int. Cl.6 .......................... G01F 1/78; G01F 1/84
[52] U.S. Cl. ................... 73/861.38; 73/861.37
[58] Field of Search ........... 73/861.36, 861.37, 861.38, 73/32 A

[56] References Cited

U.S. PATENT DOCUMENTS

| | | | |
|---|---|---|---|
| 4,192,184 | 3/1980 | Cox et al. | 73/32 A |
| 4,193,291 | 3/1980 | Lynnworth | 73/32 A |
| 4,729,243 | 3/1988 | Friedland et al. | 73/861.38 |
| 4,730,501 | 3/1988 | Levien | 73/861.38 |
| 4,738,143 | 4/1988 | Cage et al. | 73/861.38 |
| 4,793,191 | 12/1988 | Flecker et al. | 73/861.38 |
| 4,823,614 | 4/1989 | Dahlin | 73/861.38 |

*Primary Examiner*—Richard E. Chilcot, Jr.
*Assistant Examiner*—William L. Oen
*Attorney, Agent, or Firm*—Seymour Levive

[57] ABSTRACT

A system for construction of mass density sensors and mass flow sensors using modular elements to construct low cost, application optimized, sensor assemblies. The basic configuration is a mass density sensor, including a frame (13), an internal conduit (50), and a pair of integrated torquer/angular motion pickup modules (100a,b). Application specific seal modules (60a,b, 62a,b, 64a,b) are provided between the internal conduit (50) and interface ports (20a,b) on the frame (13). The internal conduit (50) is connected to the frame by a system of radial stays (90a,b) and (91a,b) and lateral stays (130a,b) and (132a,b). The pair of integrated torquer/angular motion pickup modules (100a,b) is fixed on the frame (13). Permanent bar magnets (70a,b) are fixed to the internal conduit (50). The sensor is connected to an external conduit. During operation, the internal conduit (50) is driven to oscillate in rotation relative to the frame (13). This angular motion is around a well defined rotation axis and is at the natural frequency of oscillation of the stay and internal conduit system. The instantaneous velocity of this angular motion is sensed and converted to a signal by the angular velocity sensing circuit (190). The signal is conditioned by an application-optimized circuit (230) to assure distortion-free transmission of the signal to the external system.

20 Claims, 16 Drawing Sheets

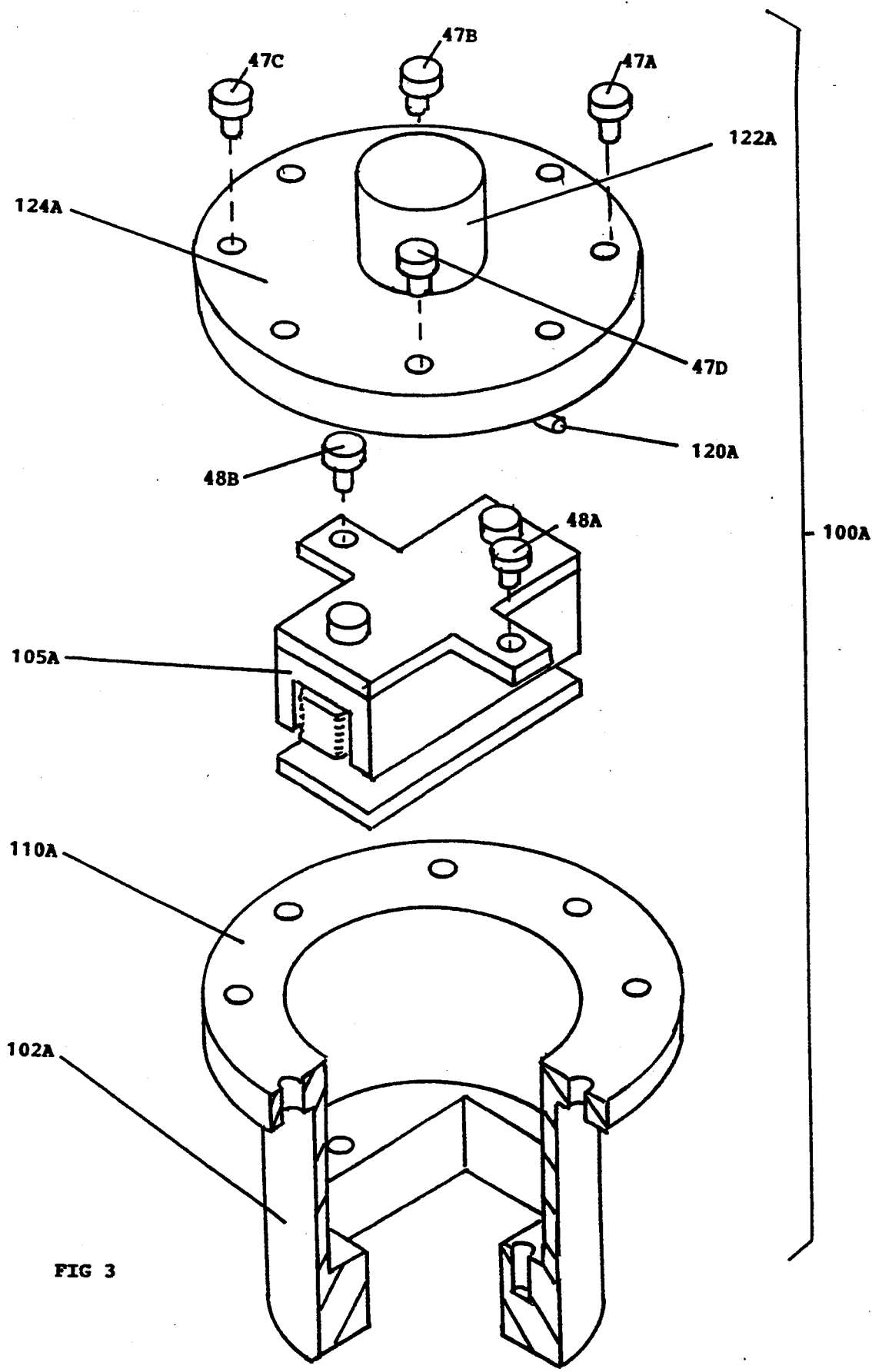

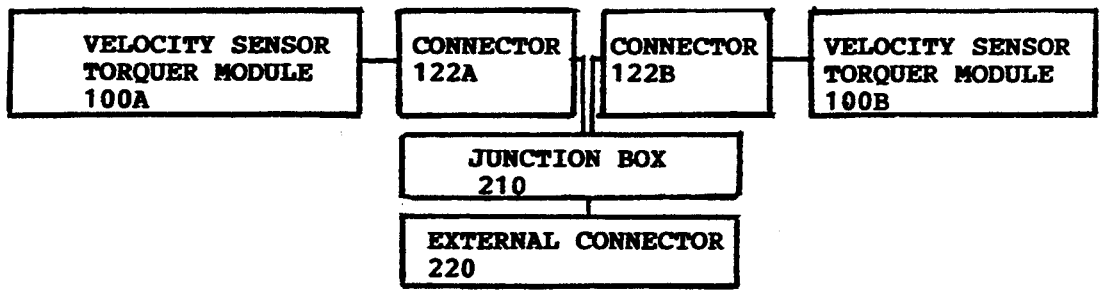
WIRE HARNESSS FOR DENSITY SENSOR CONFIGURATION 200
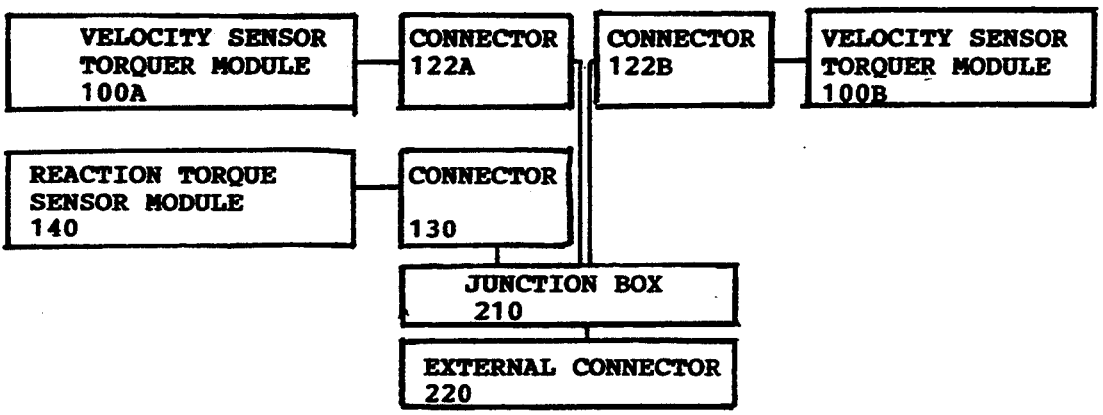
WIRE HARNESSS FOR DENSITY/ MASS FLOW SENSOR CONFIGURATION 202
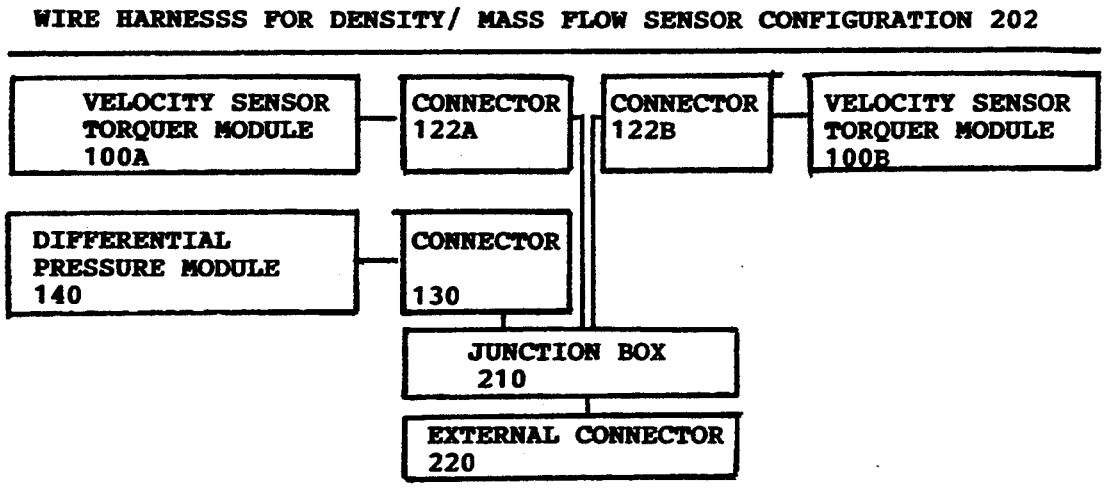
WIRE HARNESSS FOR DENSITY/ MASS FLOW SENSOR CONFIGURATION 204
FIG 10D

MODULAR SYSTEM OF LOW COST FORM OF CONSTRUCTION FOR APPLICATION-OPTIMIZED FLUENT DENSITY AND MASS FLOW SENSORS

BACKGROUND: FIELD OF INVENTION

This invention relates to a versatile, low cost form of construction for a direct-reading fluent density sensor that may;

- with the addition of a modular torque reaction detector, be used as a direct-reading fluent density and mass flow sensor, operating on gyroscopic reaction principles, or;
- with the addition of a modular volumetric flow sensor, be used as a direct-reading fluent mass density and inferential mass flow sensor, or;
- with the incorporation of an integral flow velocity sensor be used as a direct reading mass density and inferential mass flow sensor.

BACKGROUND: DESCRIPTION OF PRIOR ART

In the present state of the art (circa 1993), two major classes of fluent mass density sensors and mass flow sensors, direct or inferential, are generally recognized in the market place.

(All sensors referred to herein are used to measure the mass density and/or mass flow rate of fluids. Hereinafter, the terms density or mass density are intended to identically mean fluid mass density, and the terms flow or mass flow are intended to identically mean fluid mass flow rate.)

The prior art in each of these classes is well developed and most commercially successful manufacturers offer sensors which service specialized, hence narrow, market niches where performance differences are relatively small and competition is very keen. In such situations, the ability of a manufacturer to increase market share by offering sensors that can compete on a performance level, in many market niches, without having to offer sensors of diverse operating principles and detail designs, is of obvious economic advantage.

The novel oscillatory mass density and/or mass flow sensors that are the subject of this present patent application use the inertial reaction of matter to acceleration as the means of measurement. This characteristic limits the field of pertinent prior art to variable moment of inertia oscillatory mass density sensors and to gyroscopic or coriolis mass flow sensors.

The search of prior art found many direct reading mass flow sensors which offered mass density determination capability. The search of prior art also found many inferential mass flow sensors which offered mass density determination capability, and a smaller number of single function inferential mass flow sensors.

No system of construction for either direct reading sensors or for inferential sensors was found that exhibited the novel form of construction described herein. In addition, none offered the very high degree of modularity inherent in this novel form of construction.

This novel form of construction represents a significant improvement, in terms of cost effectiveness, over inferential or direct reading, mass density sensors and inferential or direct reading mass flow sensors with mass density capability constructed according to prior art.

GENERIC FEATURES IN THE PRIOR ART

In the prior art, two forms of mass flow meters directly measuring inertial reactions have been identified by the USPTO as gyroscopic or coriolis mass flow meters and have been assigned the classification number of 73/861.38. From 1952 to February 1992, there have been no less then 119 U.S. patents issued under this classification number. Of these patents, a great majority have been for mass flow meters utilizing at least one vibrating flow tube. Such meters have established themselves in popular usage in industry as "coriolis" meters, even though other types of mass flow meters, which also utilize the coriolis effect (such as the fuel flow rate transmitters used in aircraft and rockets) are widely used. In this document, the term "coriolis meter" will refer to the vibrating flow tube type described above.

In review of gyroscopic/coriolis mass flow sensors constructed according to the prior art, it becomes evident that the distinction between the two forms—gyroscopic and coriolis—is not sharp, and that many of the features of mass flow meters which are dubbed "coriolis meters" in the current literature were incorporated in the design of "gyroscopic mass flow meters" patented as late as 1966. (See USPTO U.S. Pat. No. 3,276,257.)

In both forms of construction, an internal conduit oscillates. If the oscillation is at the natural frequency of the internal conduit, this natural frequency will vary as a function of the density of the matter in the conduit, and the density of the matter can be determined independent of the flow rate. In both forms, the instrumentation used for measurement of motion response of the internal conduit yields signals which have the frequency of motion as an integral component.

However, there are significant features which distinguish between the two forms of flow meter:

a) in the gyroscopic form, an internal conduit rotates or oscillates as a whole relative to the frame of the meter; in the coriolis form, the internal conduit (or conduits) flexes or bends relative to the frame of the meter, b) in the gyroscopic form, the gyroscopic couple due to the inertial reaction of the fluent flowing in the internal conduit is measured directly; in the coriolis form, the coriolis forces due to the inertial reaction of the fluent flowing in the internal conduit act to modulate the motion response of the flexing internal conduit and this change in motion response is used as the measure of the inertial reaction, In the coriolis form of the commercially successful mass flow meters constructed according to the prior art, the physical characteristics of the material from which the internal conduit is made directly affect the motion response of the conduit. Specifically, the tensile, compressive and torsional elastic moduli are significantly involved in the response. This interaction between the function and material limits the freedom of the practical design and hence drives up the cost of coriolis meters of the vibrating tube type.

In the previous art, inventors configured sensor devices for mass flow/density measuring means as stand-alone meters. This approach required that each meter have not only the functional sensor means for measuring the quantities required to determine the mass flow rate of the fluent, but also have analog or digital computing elements, control elements and display elements. These elements can be remote from the primary sensor. Given the present (circa 1993) state of digital computing and electronic control and display technology, these functions can often be more economically performed by a central, shared facility serving several mass flow meters, or by a central control system that may exist for other reasons as well. The cost of each primary sensor constructed according to the system described herein is thus lower than the stand-alone meters used in prior art.

SPECIFIC FEATURES IN THE PRIOR ART

Aside from these generic considerations, there are many other features of mass flow meters constructed according to the prior art that tend to raise the cost of these meters.

(A) Some gyroscopic mass flow/density sensors which utilize oscillatory rotation of the sensor internal conduit use rubbing contact seals to allow the sensor internal conduit to rotate as a whole relative to the fixed member of the frame in which the sensor conduit is installed. Seals of the performance and reliability needed raise the cost.

(B) Some gyroscopic mass flow/density sensors which utilize oscillatory rotation of the sensor conduit use flexing bellows to accommodate the internal conduit motion relative to the fixed member of the frame in which the internal conduit is installed. The flexing element raises the cost and lowers the reliability of the sensor.

(C) Some gyroscopic mass flow/density sensors which utilize oscillatory rotation of the sensor conduit utilize structural members between the case of the meter and the sensor conduit. These members act as virtual "gimbal rings". (See USTPO U.S. Pat. No. 3,108,495 for a well-described example of this prior art.) The inertia of these structural members is added to that of the sensor conduit. The size and cost of the mass flow meter is thereby raised.

(D) In the type of gyroscopic mass flow/density meters referred to in paragraph (C) above, relative angular motion between the "gimbal rings" is controlled by flexure pivots, rolling bearings or rotary journal bearings. These pivot action means raise the cost and decrease the reliability of the oscillatory meters constructed according to this prior art.

E) In the coriolis mass flow meters, pressurized internal conduit sections in the sensor are firmly affixed to a frame and are driven to oscillate relative to the frame. (See USTPO U.S. Pat. Nos. 3,365,944, 4,127,028, 4,187,721, 4,491,025, 5,060,523 and 5,069,075 for typical examples.) This construction is also used in the Dynatrol ® cell.

(In the review of the prior art, the search found only one example of a mass density sensor operation on a direct inertial reaction principle, the Dynatrol ® Cell CL-10TY series, a product of Automation Products Inc., Texas, Patents Pending. This device shares many costly design features in common with the coriolis mass flow sensors discussed in paragraphs E, F and I of this section. Therefore, the discussion in these paragraphs of previous art in regard to coriolis mass flow sensors also covers mass density sensors of the Dynatrol ® type.)

The oscillatory motion causes fluctuating stress to be superimposed on the wall stress induced in such conduit sections due to internal pressure, regardless of the flow rate of the matter inside the sensor section. These fluctuating stress conditions mentioned above limit the choice of materials of construction for the sensor element of coriolis effect devices to highly alloyed, high fatigue strength materials. These materials (316L, Hastaloy C for example) are expensive and need costly skill and care to fabricate.

Similar considerations effect the design and manufacture of the flexing bellows used in gyroscopic flow meters which utilize vibratory drives. The difficulty encountered in satisfactory manufacture of these components is attested to by the high prices charged by the few companies that offer bellows for sale on the open market.

(F) In the coriolis mass flow sensors, internal conduit sections in the sensor elements are firmly affixed to a frame and are driven to flex relative to the frame. When matter flows during sensor operation, these sections of internal conduit in the sensor elements flex relative to each other as well as to the fixed frame.

This relative flexure is due to the inertial reaction forces exerted on the flexing conduit by the flow stream, which forces vary as a function of the mass flow rate of the flow stream. These reaction forces cause the motion response of the internal conduit to vary in a manner determined by the elastic characteristics of the material and the geometric form used for the internal conduit.

If the elastic characteristics of the material used in the internal conduit are not constant under all conditions of temperature and pressure encountered in operation, the calibration of the instrument will be unstable and compensation elements must be added to the meter. This problem also exists in the Dynatrol ® cell.

Internal conduit temperature sensors and associated electronics are now used by leading manufacturers to correct for this effect (see Control Engineering, August 1985, pp. 77–79 for quotation from E. Dahlin, President of EXAC Corp.). These elements add to the cost of the meter.

(G) In reviewing stand-alone mass flow meter systems of the gyro/coriolis type, it is clear that a share of the manufacturing cost of such systems lies in the sensor controls and the signal processing elements, i.e., data acquisition, data conditioning, computation, external system interface and man/machine interface circuits and devices. These costs recur in the cost of each of the individual meters.

(H) In the prior art, costly servo feedback systems, with varying degrees of complexity have been used to control the sensor conduit drive.

(I) In the coriolis meters of the contemporary flow tube type, erosion or corrosion of the walls of the internal conduit carrying the fluent will cause the effective spring constant of the internal conduit to change, thus effecting the stability of calibrations. The increased frequency of calibration is costly to the user of the instrument.

(J) In the coriolis meter as used in the prior art, the same relatively costly motion-sensitive pickups and their relatively complex supporting electronics are used to determine both the density and the mass flow rate of the matter in the flow tube. However, there are many applications where the flow rate determination is not required; in these markets, the higher cost imposed by the dual purpose instrumentation is an economic handicap.

(K) The manufacturers of the coriolis flow sensors identified by patent number in this discussion (see E above), and other manufacturers in this field, usually list gases and vapors as suitable for such devices. However, in actual fact, coriolis sensors of such configurations are not often used in such service.

For example, AABK-FLOW Inc., a leading manufacturer of such coriolis sensors, lists almost five hundred substances which are metered by their coriolis device. Of these, the great majority (99%) can be identified as liquids.

Further, SIERRA INSTRUMENTS INC., a leader in the manufacture of thermal gas mass flow sensors, in its promotional literature makes the statement: "The only other direct reading mass flow sensors—coriolis sensors—are applicable to slurries and liquids, and do not have sufficient sensitivity for gases".

While it is not claimed that prior state of the art coriolis sensors are completely unsuited for gases, it is clear that such sensors are at a severe competitive disadvantage in the large, lucrative market for mass flow metering of gases.

OBJECTS AND ADVANTAGES

It is the object of this invention to provide a low cost sensor of modular design that may be configured as a mass density sensor, or as an inferential mass flow and mass density sensor, or as a gyroscopic mass flow and mass density sensor; each configuration being assembled from a limited number of modular elements.

(A) It is a further object of this invention to provide a gyroscopic mass flow or density sensor that will not require rubbing contact seals.

(B) It is a further object of this invention to provide a gyroscopic mass flow or density sensor that will not require flexing bellows-like members to be inserted in the sensor flow conduit.

(C) It is a further object of this invention to provide a gyroscopic mass flow or density sensor without relatively massive and expensive support members (gimbals) interposed between the internal conduit and the stationary structure to which the internal conduit is connected.

(D) It is a further object of this invention to provide a gyroscopic mass flow or density sensor without flexure pivots, rolling bearings or journal bearings.

(E) It is a further object of this invention to provide a gyroscopic mass flow or density sensor in which fluctuating stresses incident to the operation of the gyroscopic mass flow/density sensor are effectively confined to portions of the sensor internal conduit which are not affected by inertial reaction forces and/or to parts of the sensor which are not part of the internal conduit.

(F) It is a further object of this invention to provide a gyroscopic mass flow or density sensor in which the elastic constants of the materials which are used in the sensor flow conduit do not effect the calibration or output of the instrument.

(G) It is a further object of this invention to provide a baseline sensor that will generate signals representing the angular velocity of the internal conduit within the sensor, and to provide additional signals representative of gyro reaction torque.

(H) It is a further object of this invention to provide a sensor conduit that will oscillate in a stable manner at its natural frequency of oscillation upon application of AC or DC power from an external source without requiring a servo feedback system.

(I) It is a further object of this invention to provide a gyroscopic mass flow sensor in which erosion of the walls of the sensor internal conduit will not effect the calibration of the sensor.

(J) It is a further object of this invention to provide a low cost, baseline sensor configured only as a density sensor, that can be reconfigured as a combined mass flow and density sensor with a minimum addition to the baseline configuration, i.e., one that conserves the parts and the arrangement of parts in the baseline sensor.

(K) It is a further object of this invention to provide a mass density and/or mass flow sensor that will operate reliably and with satisfactory accuracy when used with gases, vapors and multiphasic low density states of matter.

It is clear that the modular nature of the system of construction as described and discussed in this patent application document allows for a very large number of practical configurations of the sensor. These practical configurations will depend on the specific application in which the sensor is intended to be used.

Such a situation is common when configuring modular systems of all types, and poses no difficulty of apprehension, or barrier to understanding, to those skilled in the appropriate arts. Such persons will be able to construct all practical configurations of the sensors described herein, using the information given herein, as is required by the specific application in which the sensor is intended to be used.

These and other objects and advantages of the present invention will no doubt become apparent to those skilled in the art after having read the following detailed description of the preferred embodiments which are illustrated in the several figures of the drawings. Further, any of the features explained above or below can be used alone, or in the combinations specifically described or in any other conceivable combination without thus exceeding the scope of the present invention. In addition, wherever the present description refers to "signals", they may be either analog or digital signals.

(Part numbers, when underlined, indicate that the device referred to is an assembly of distinct parts, each identified with its own part number.)

Figure 1:
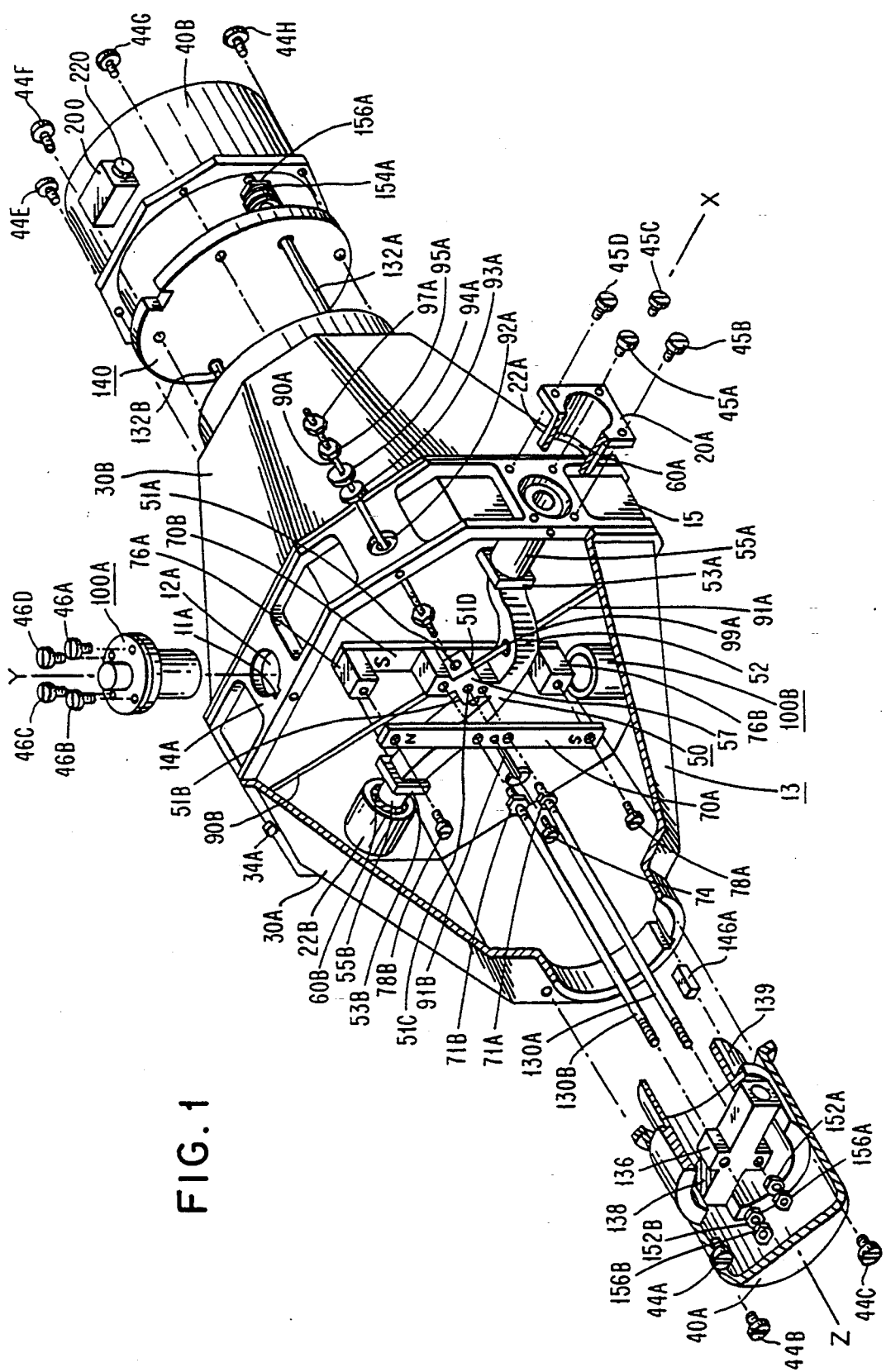
FIG. 1 is a view of the preferred embodiment of the mass flow/density sensor unit configured for the flow of matter in either direction through the sensor, with flexible impermeable barriers 60a and 60b used to contain the matter traversing through the internal conduit 50. The view is taken looking down at the left side of the mass flow/density sensor which is exploded primarily along the z axis.
Figure 1A:
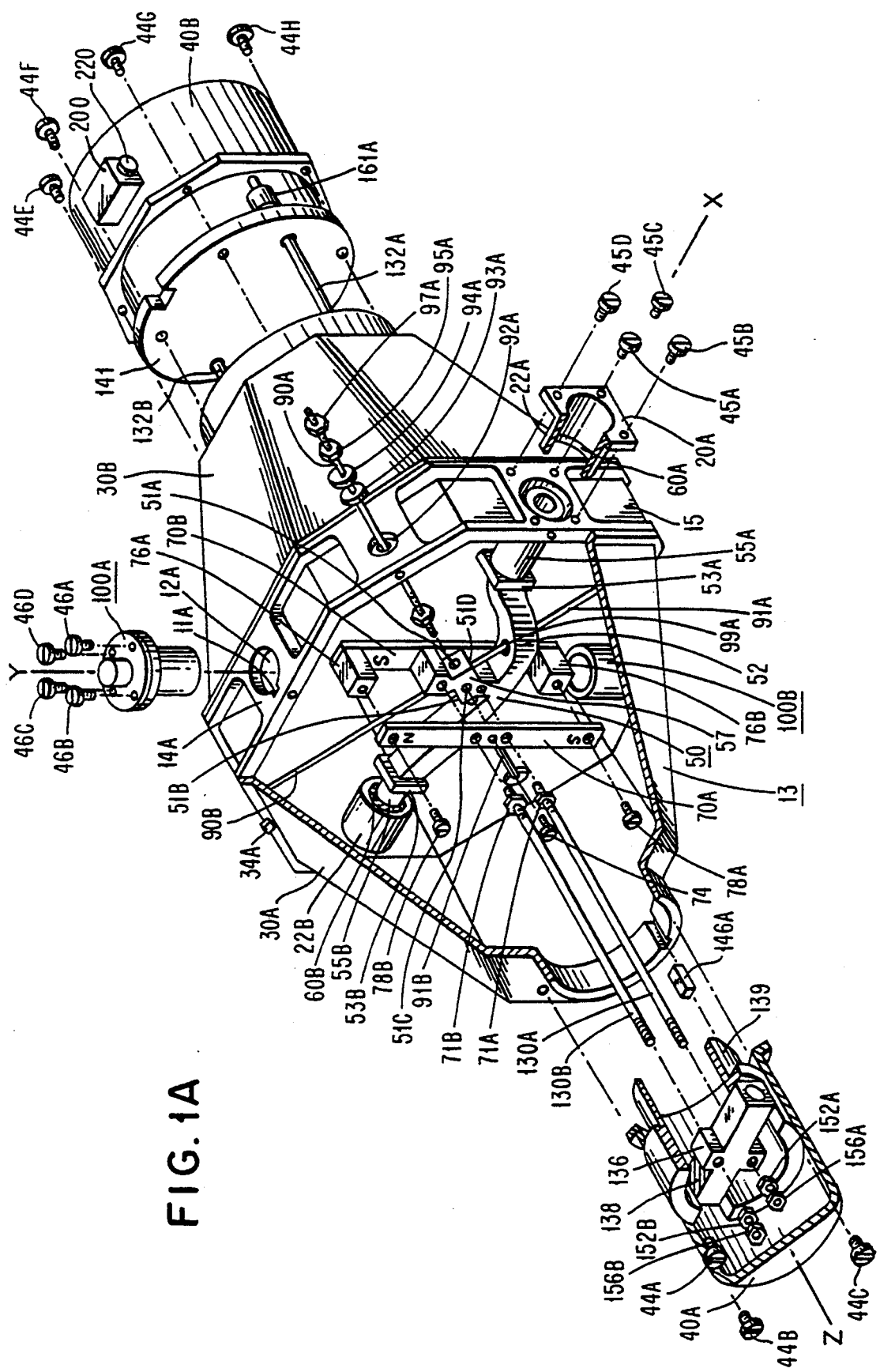

FIG. 1A is a view of the preferred embodiment of the density sensor unit configured for the flow of matter in either direction through the sensor, with flexible impermeable barriers 60a and 60b used to contain the matter traversing through the internal conduit 50. The view is taken looking down at the left side of the density sensor which is exploded primarily along the z axis.

Figure 2:
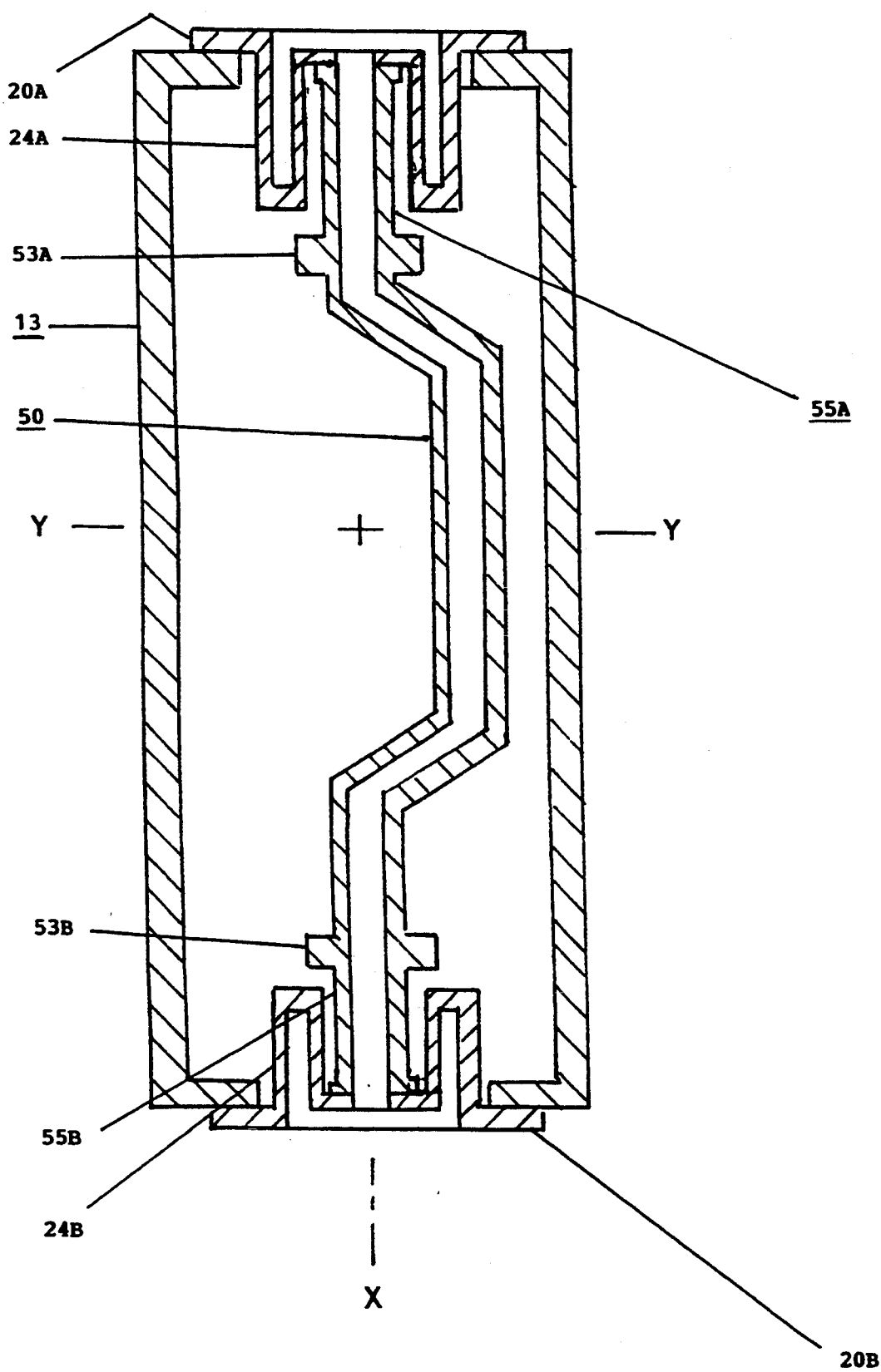

FIG. 2 is a schematic of the preferred embodiment of the mass flow/density sensor unit configured for the flow of matter in either direction through the sensor, utilizing elastic sections 24a and 24b to which are directly connected to the internal conduit 50, to contain the matter traversing between the ports 20a and 20b.

Figure 2A:
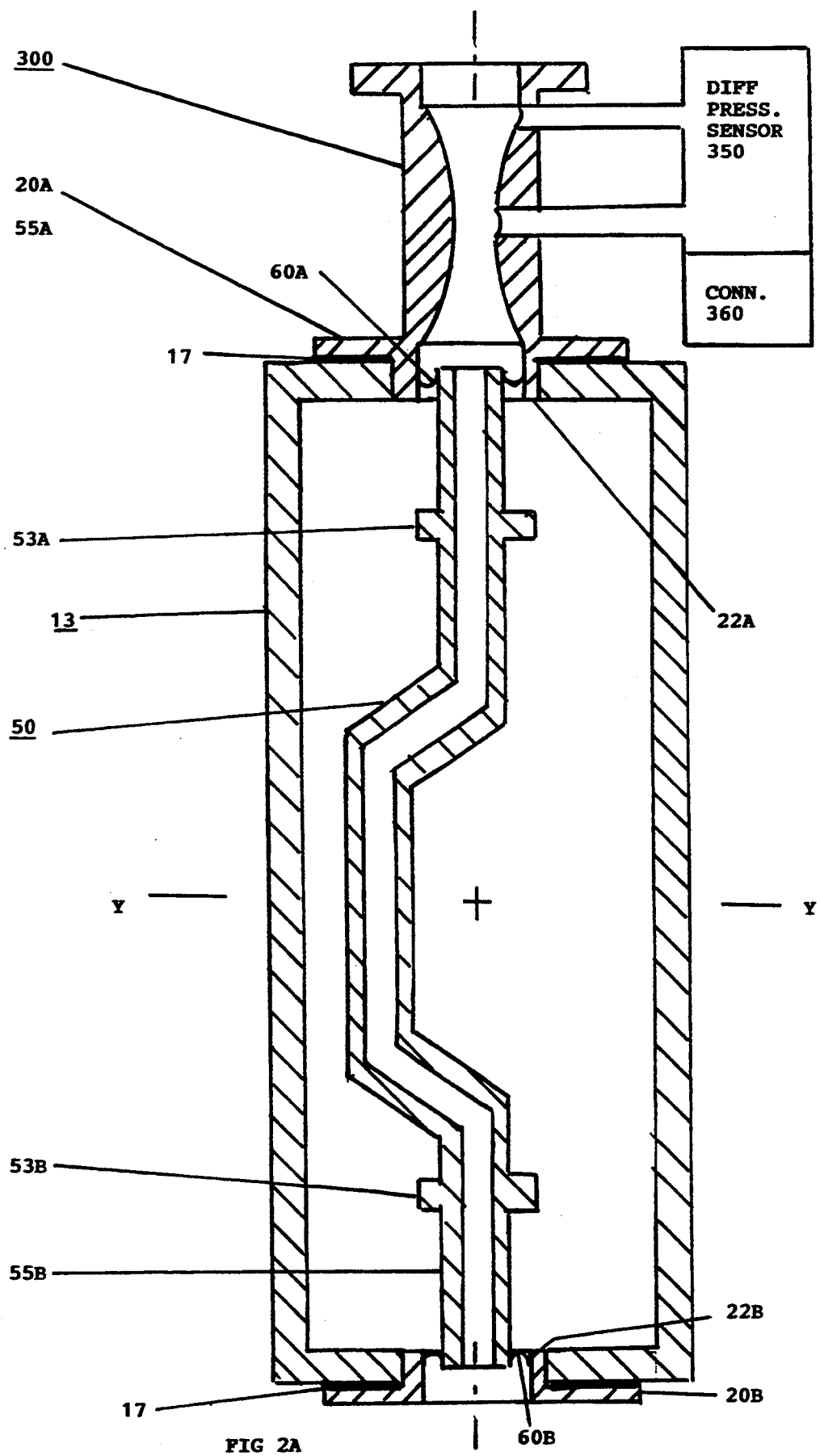

FIG. 2A is a schematic of the preferred embodiment of the inferential mass flow sensor unit formed by the addition of a modular volumetric flow rate sensor in series with the density sensor unit shown in FIG. 1A. This embodiment uses impermeable seals 60a,b between the conduit extensions 55a,b and the port extensions 22a,b to contain the matter traversing the internal conduit 50.

Figure 2B:
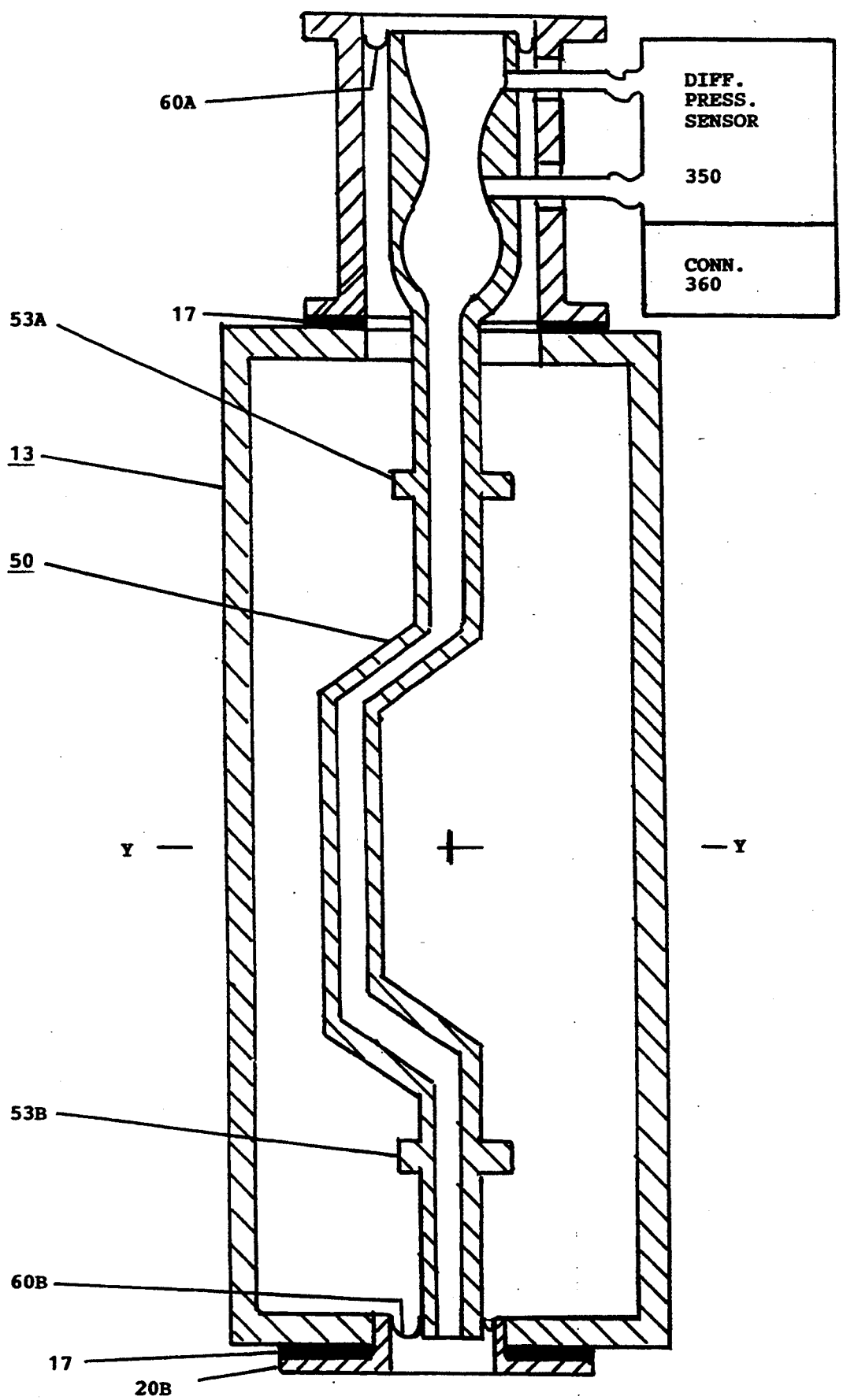

FIG. 2B is a schematic of the preferred embodiment of the inferential mass flow sensor unit formed by the addition of a fluent velocity sensor section integral with the internal conduit 50. This embodiment uses impermeable seals 60a,b between the internal conduit 50 and the port extensions 22a,b to contain the matter traversing the internal conduit 50.

Figure 2C:
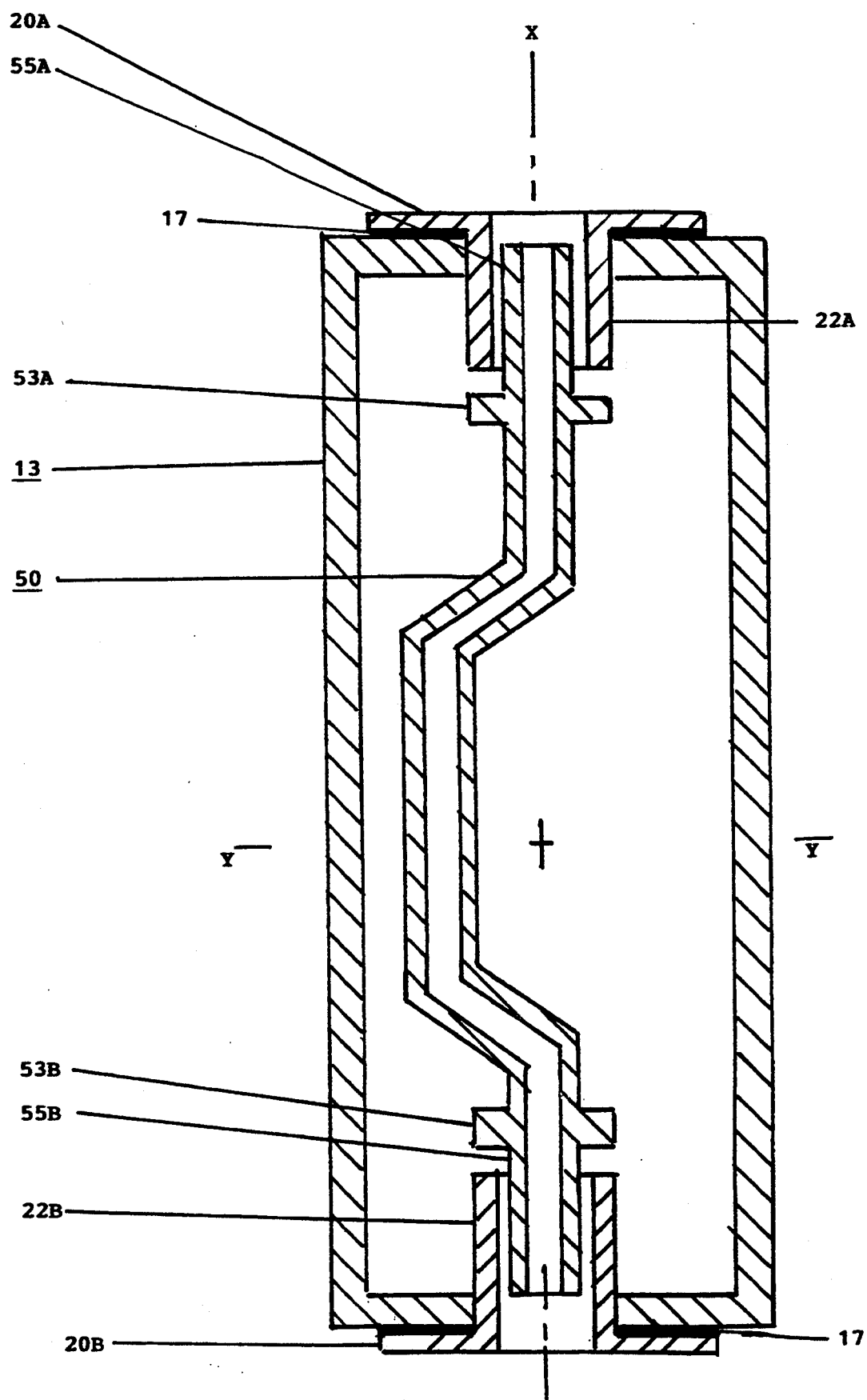

FIG. 2C is a schematic of the preferred embodiment of the sensor unit configured for the flow of gases or vapors in either direction through the sensor. This embodiment uses labyrinthine seals between the internal conduit 50 and the ports extensions 22a,b to control the escape of matter traversing the internal conduit 50. This embodiment uses a frame 13, constructed of impermeable material which is sealed by the use of joint sealing compound 17 as required to seal the joints in the frame 13.

Figure 2D:
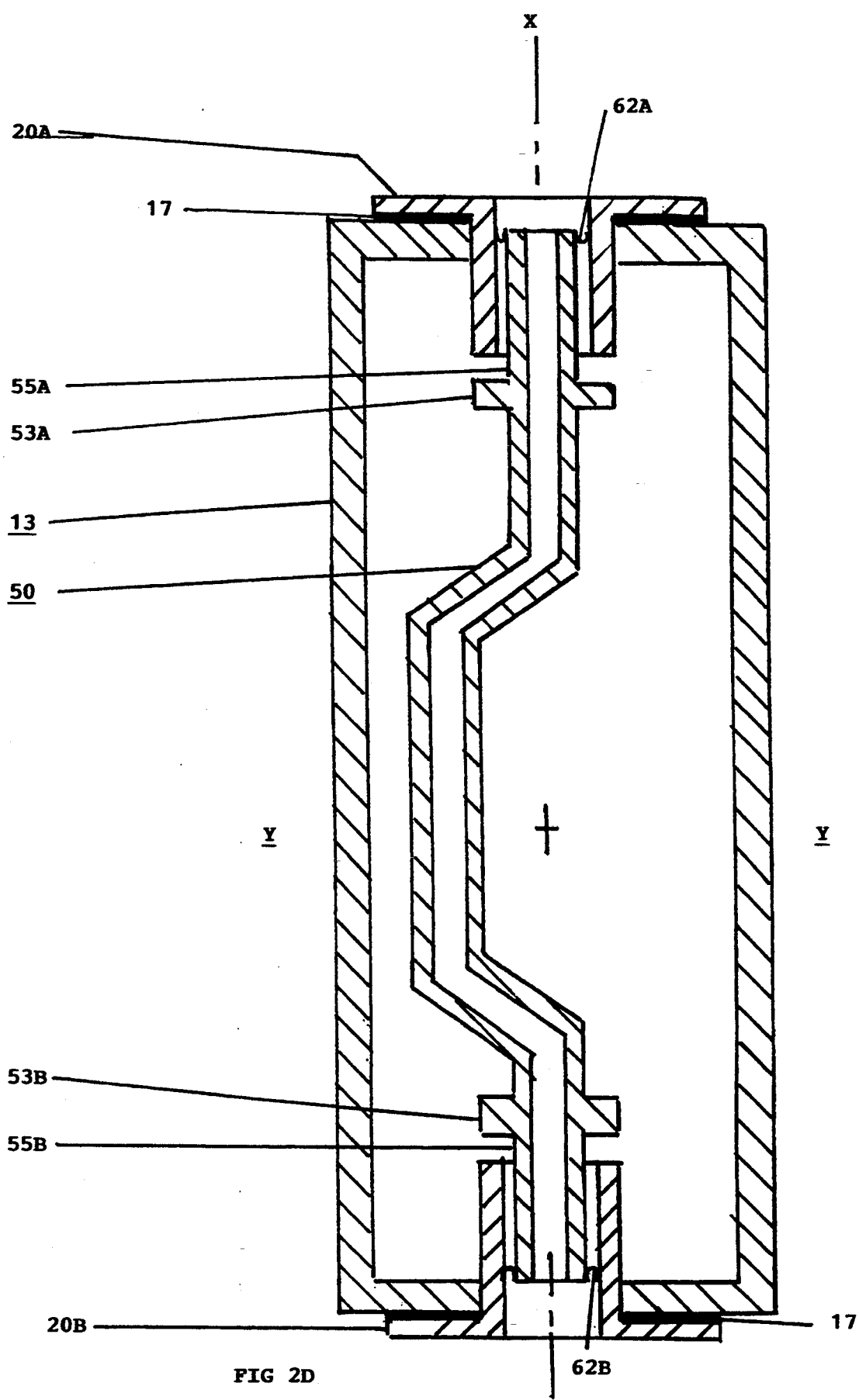

FIG. 2D is a schematic of an alternative embodiment of the sensor unit configured for the flow of gases or vapors in either direction through the sensor. This embodiment uses permeable seals 62a,b between the internal conduit 50 and the port extensions 22a,b to control the escape of matter traversing the internal conduit 50. This embodiment uses a frame 13, constructed of impermeable material which is sealed by the use of joint sealing compound 17 as required to seal the joints in the frame 13.

FIG. 3 is a view of velocity sensor-torquer module 100a exploded along the y axis.

Figure 4:
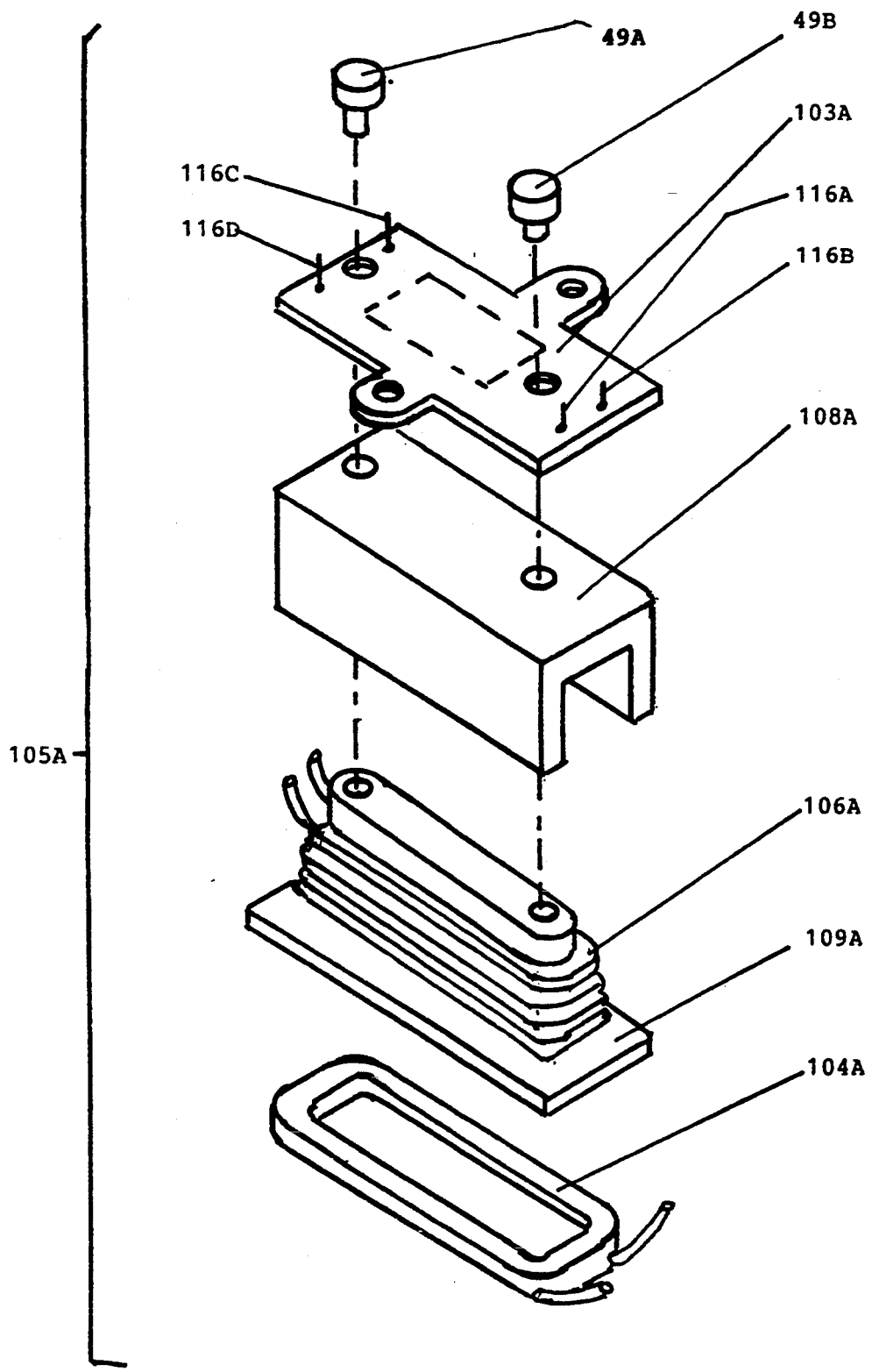

FIG. 4 is a view of the board and keeper assembly 105a exploded along the y axis.

Figure 5:
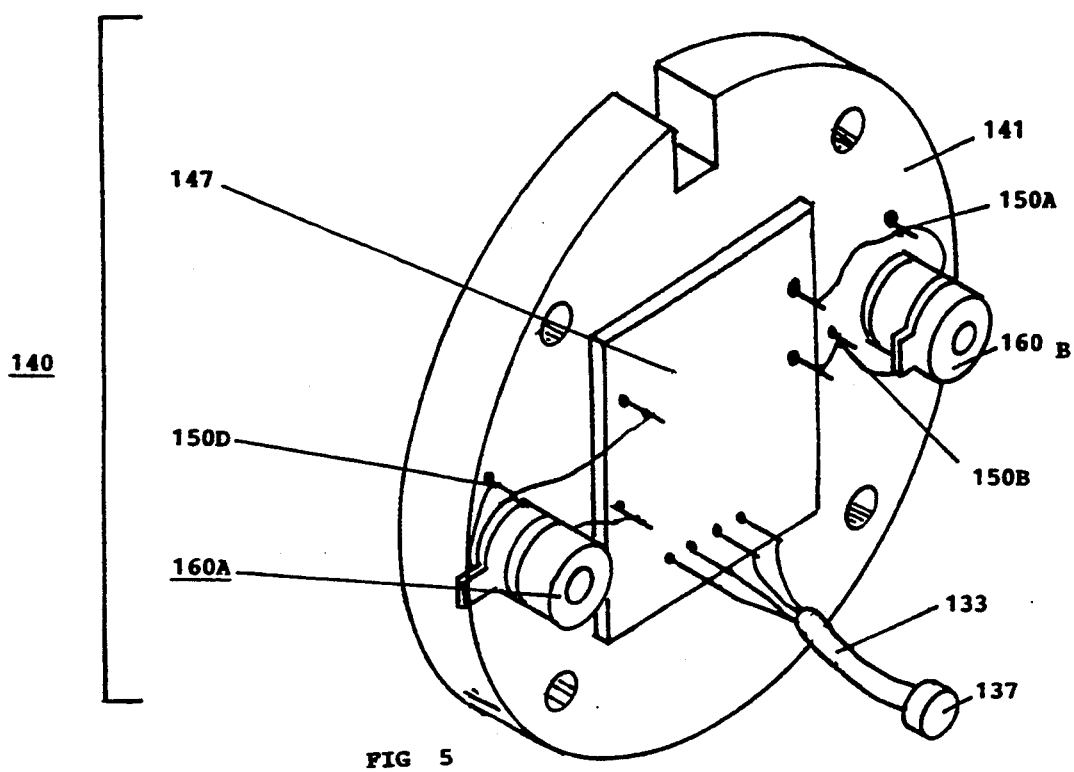

FIG. 5 is a view of the assembly of the reaction torque sensor module 140.

Figure 6:
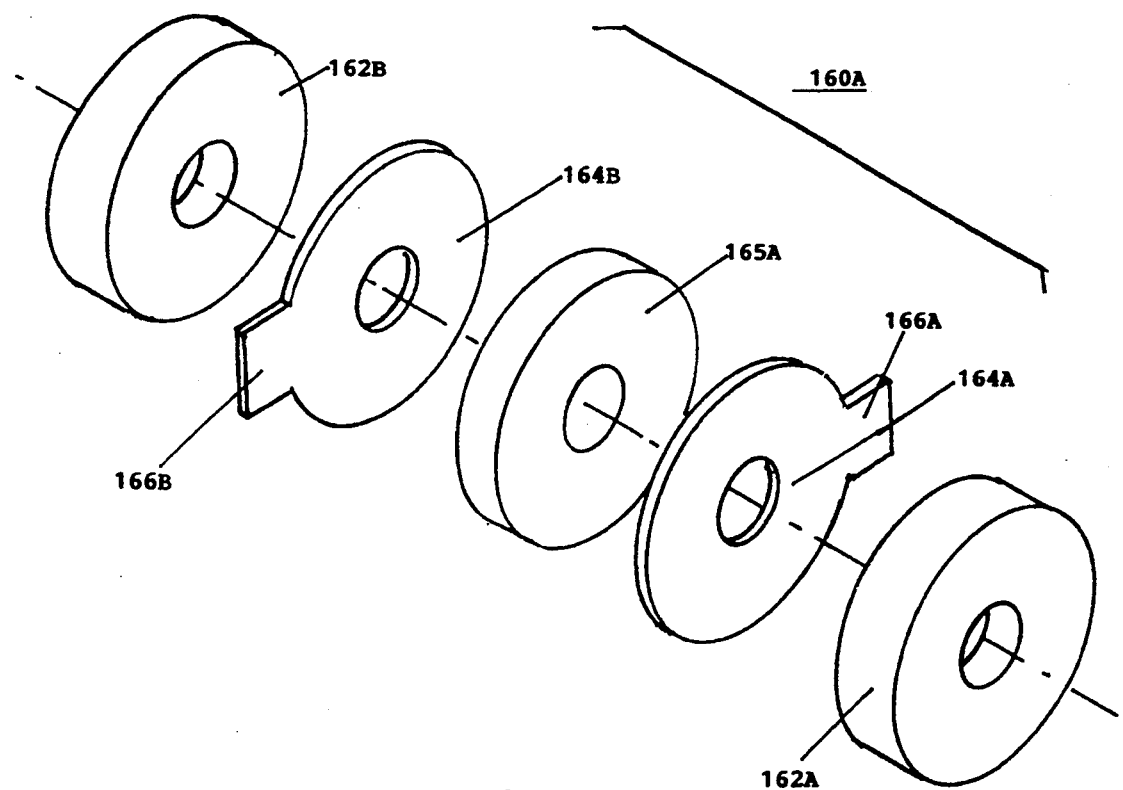

FIG. 6 is an exploded view of the bonded, polarized washer 160a.

Figure 7A:
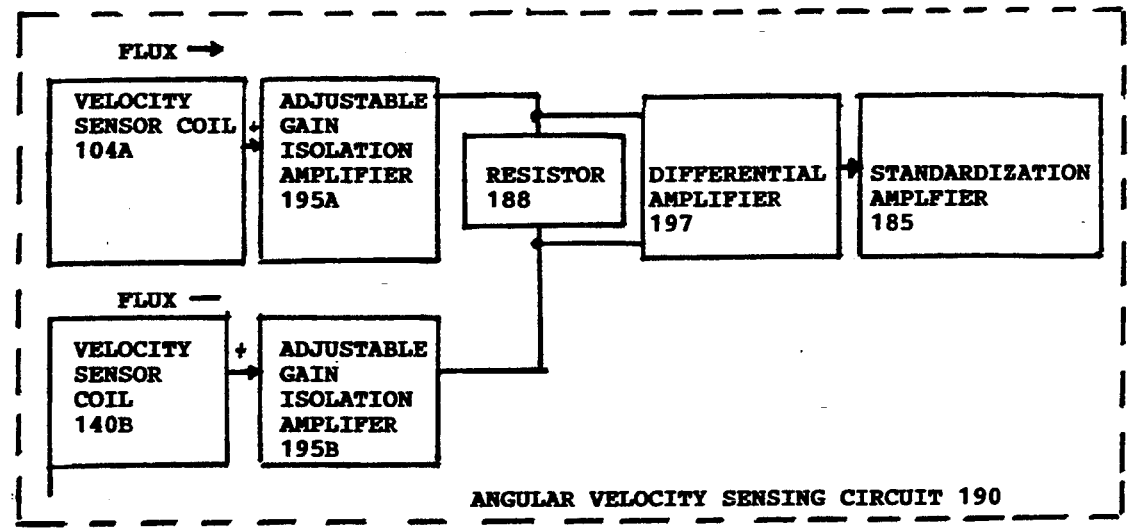

FIG. 7A is a functional block diagram of the angular velocity sensing circuit 190.

Figure 7B:
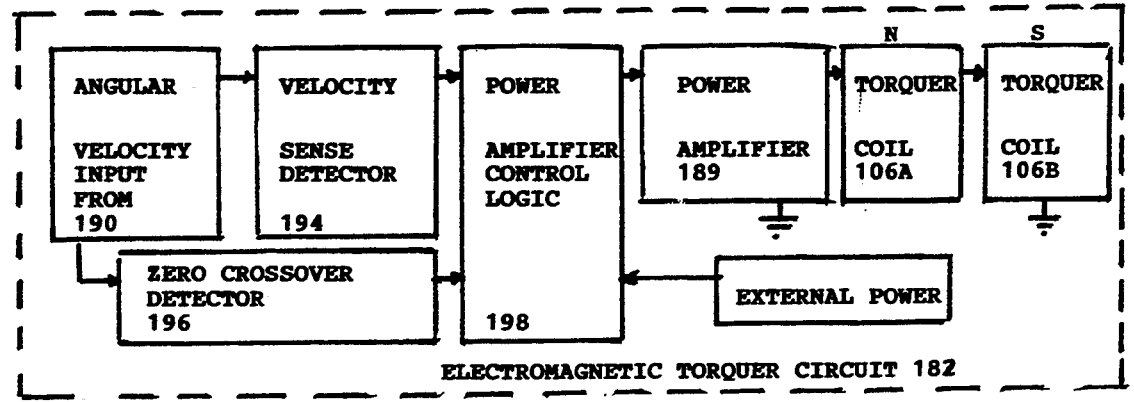

FIG. 7B is a functional block diagram of the torquer circuit 182.

Figure 8:
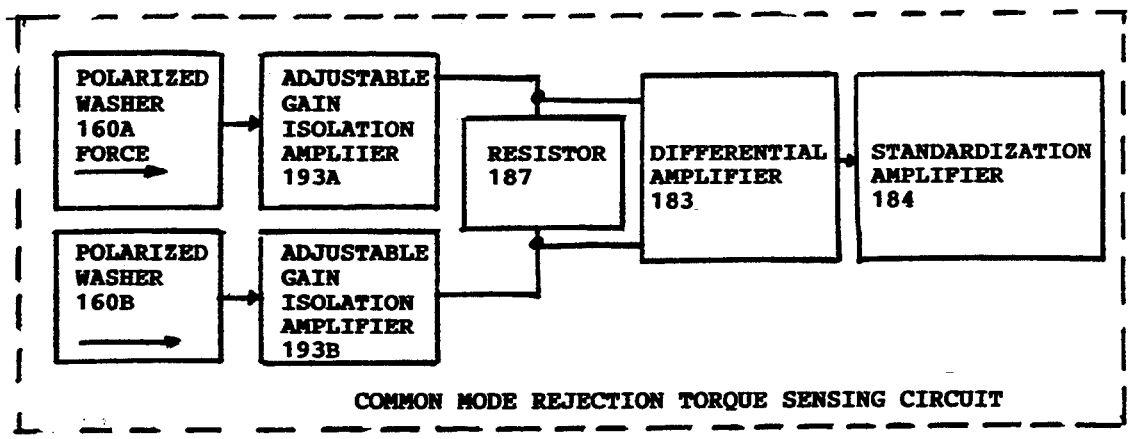

FIG. 8 is a functional block diagram of the torque sensing circuit 181.

Figure 9:
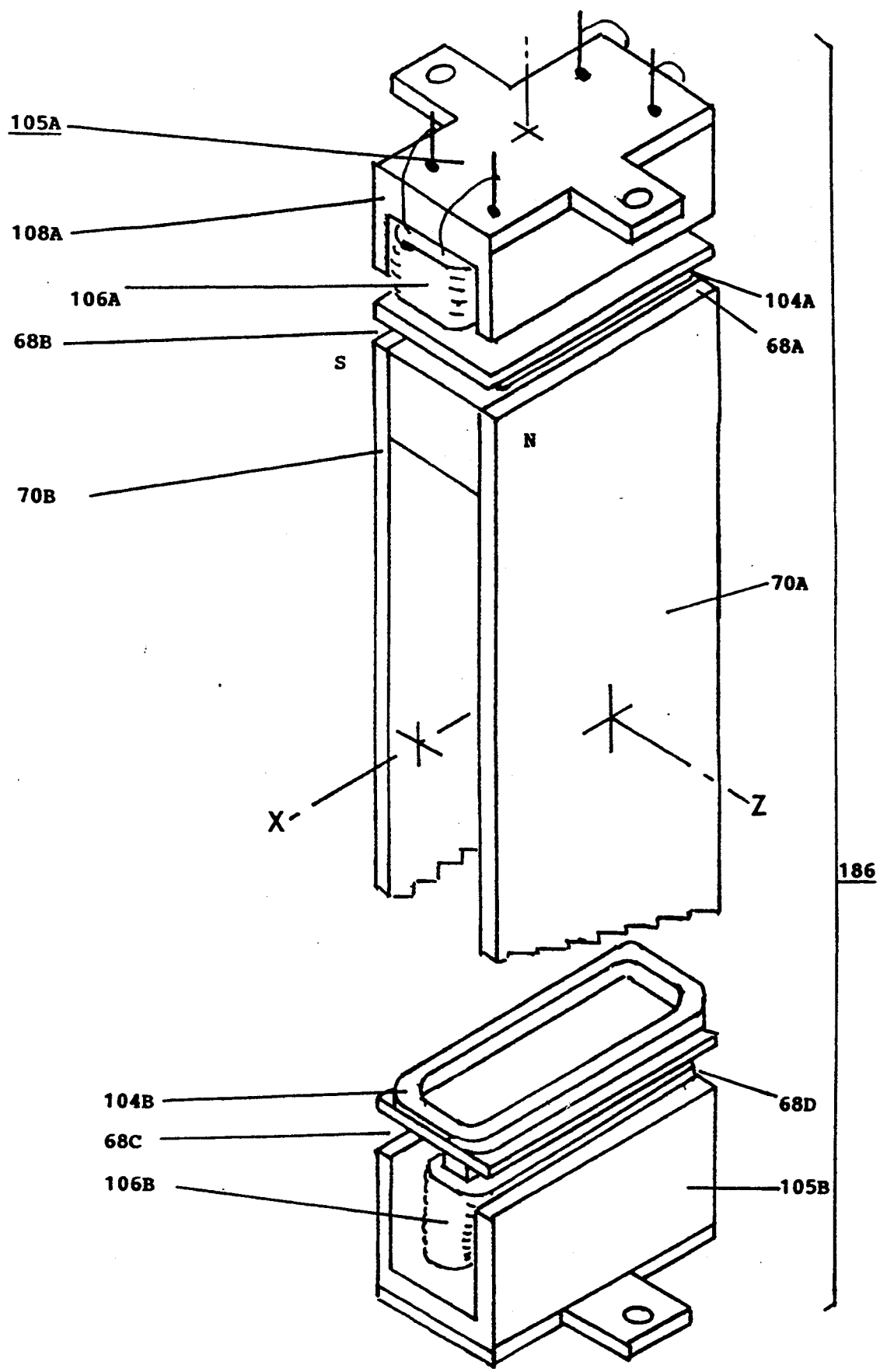

FIG. 9 is a schematic diagram of the permeable elements of the magnetic circuit 186, indicating the location of the air gaps 68a, b, c and d in the magnetic circuit 186; and the location of the torquer coils 106a,b and the velocity sensor coils 104a,b in relation to the air gaps.

Figure 10A:
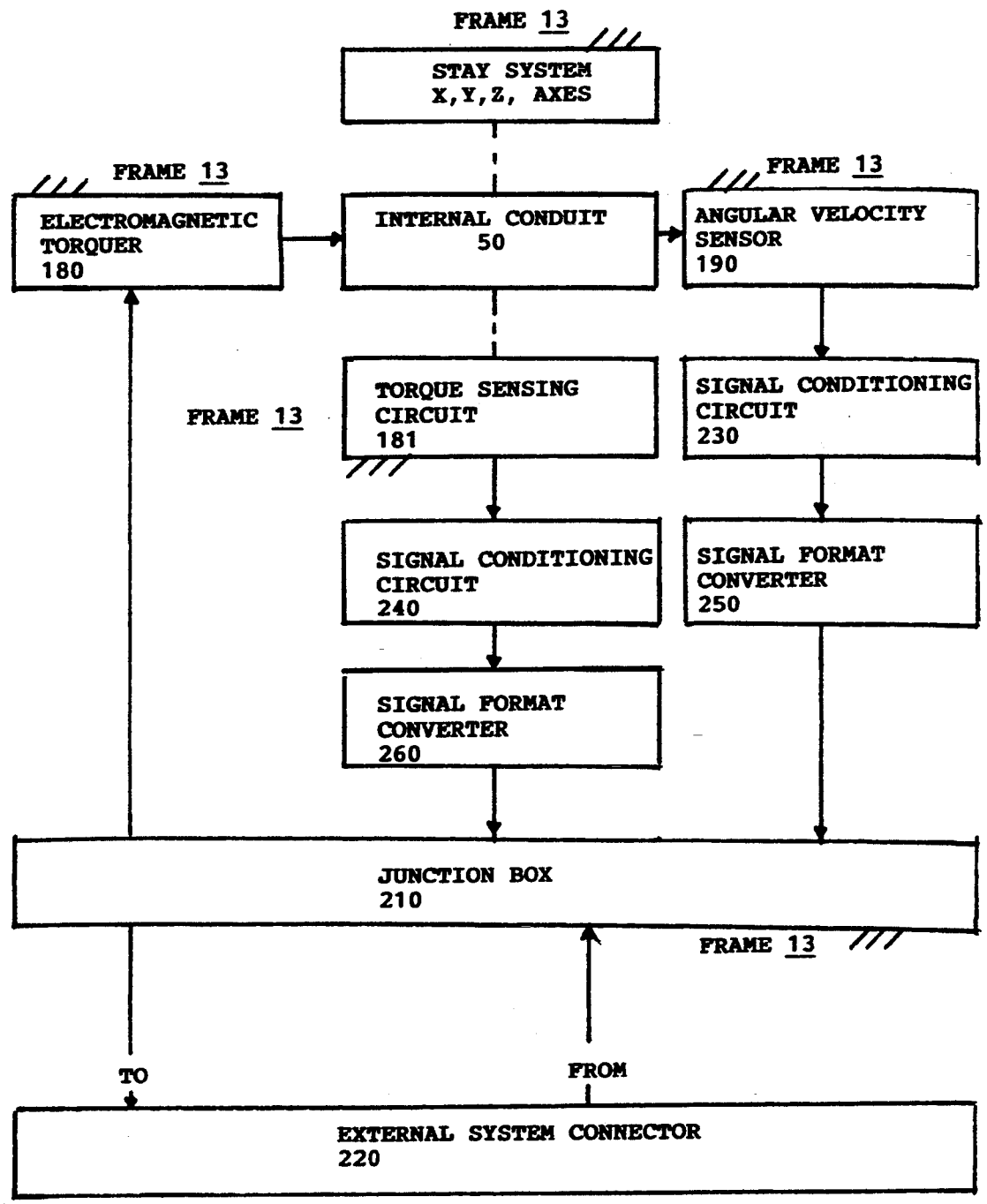

FIG. 10A is a functional block diagram of the sensor configured as a gyroscopic mass flow/density sensor.

Figure 10B:
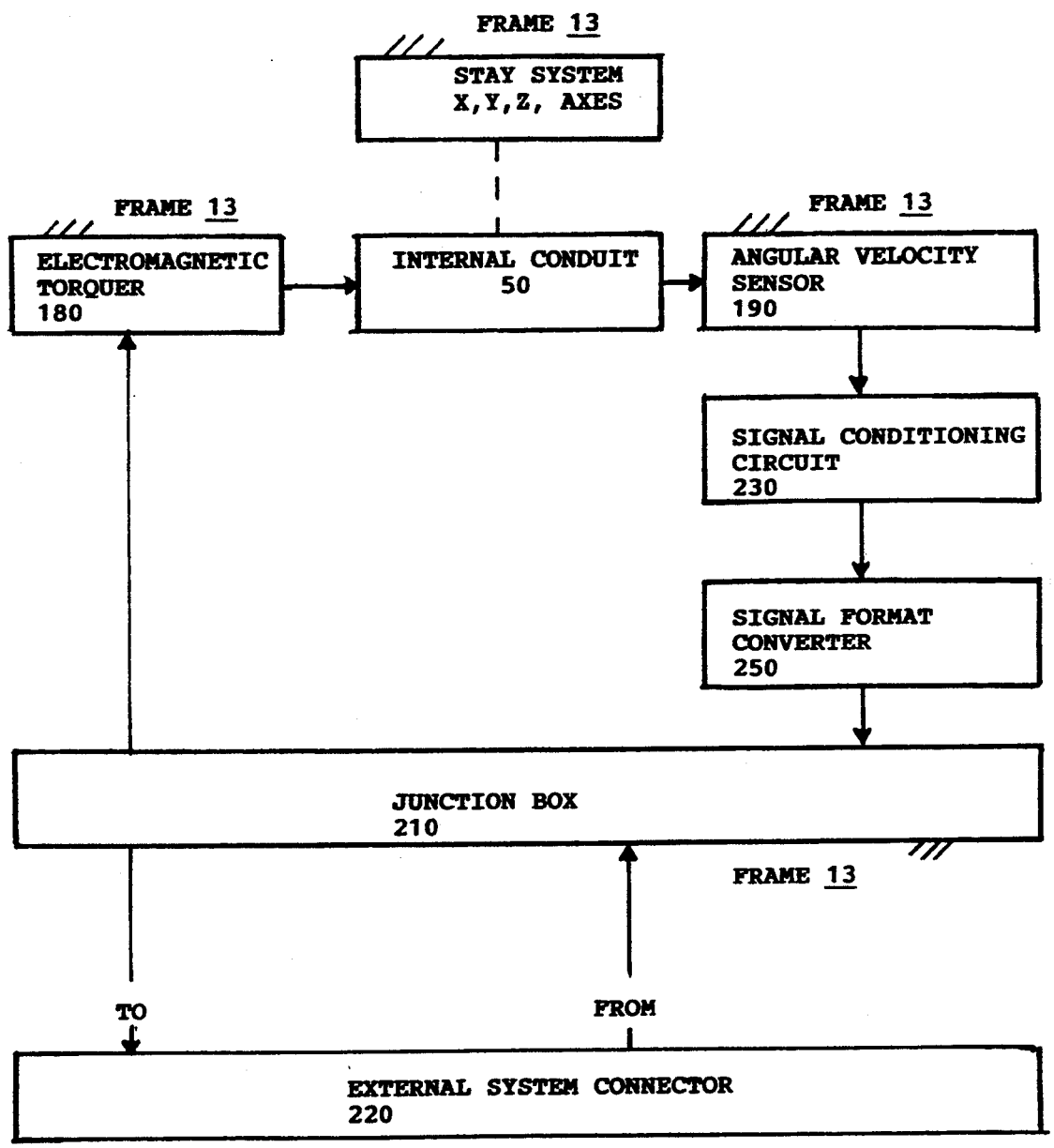

FIG. 10B is a functional block diagram of the sensor configured as a density sensor.

Figure 10C:
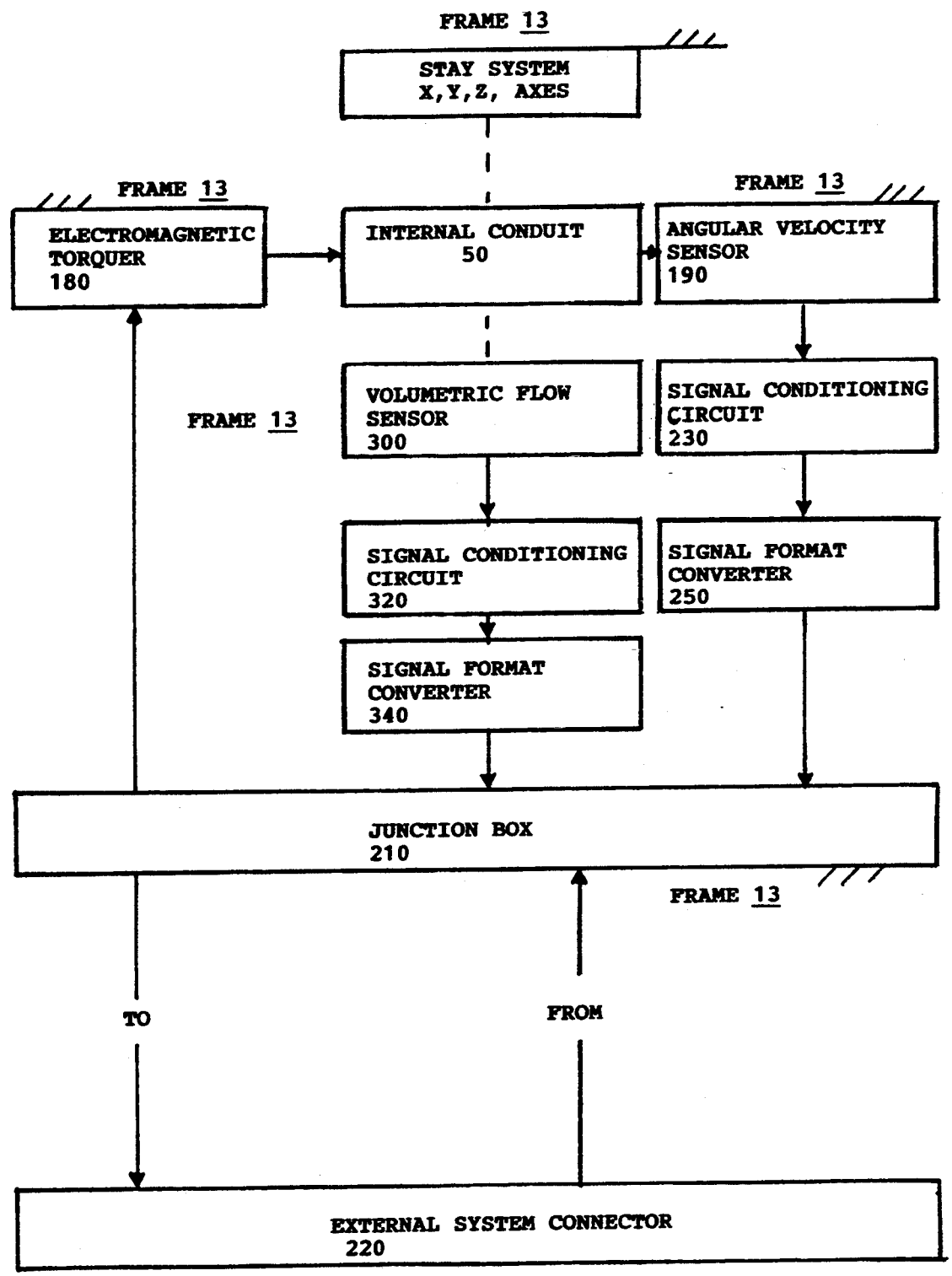

FIG. 10C is a functional block diagram of the sensor configured as an inferential mass flow/density sensor using a fluent velocity sensor. (The functional block diagram of the sensor configured as an inferential mass flow/density sensor using a volumetric flow rate sensor would be similar.)

FIG. 10D shows block diagrams of the various wiring harnesses of the sensor assemblies indicated in FIGS. 10A, 10B and 10C.

PARTS LIST

| NOMENCLATURE | PART NO. |
| --- | --- |
| key slot | 11a,b |
| through bore | 12a,b |
| frame, vessel, or housing | 13 |
| mounting pad | 14a,b |
| perimetral member or base | 15 |
| joint sealing compound | 17 |
| ports, flanges, or couplings | 20a,b |
| port extension | 22a,b |
| transition section | 24a,b |
| housing, cone or support structure | 30a,b |
| fasteners | 34a,b,c,d,e,f,g,h |
| cap or cover | 40a,b |
| fasteners | 44a,b,c,d,e,f,g,h |
| fasteners | 45a,b,c,d |
| fasteners | 46a,b,c,d |
| fasteners | 47a,b,c,d,e,f,g,h |
| fasteners | 48a,b,c,d |
| fasteners | 49a,b,c,d |
| internal conduit | 50 |
| anchor pad (part of 57) | 51a,b,c,d |
| inertial reaction duct (part of 50) | 52 |
| anchor collar (part of 50) | 53a,b |
| conduit extension (part of 50) | 55a,b |
| cruciform bar (part of 50) | 57 |
| impermeable flexible seal | 60a,b |
| permeable flexible seal | 62a,b |
| impermeable elastic seal | 64a,b |
| magnetic circuit air gap | 68a,b,c,d |
| permanent bar magnet | 70a,b |
| locking nut | 71a,b |
| central rivet | 74 |
| non-magnetic end spacer | 76a,b |
| end clamp rivet | 78a,b |
| radial stay | 90a,b |
| radial stay | 91a,b |
| anchor pad (part of 15) | 92a,b,c,d |
| self aligning washer | 93a,b,c,d |
| self aligning washer | 94a,b,c d |
| adjusting nut | 95a,b,c,d |
| locking nut | 97a,b,c,d |
| clearance pass-through | 99a,b |
| velocity sensor - torquer module | 100a,b |
| housing (part of 100a,b) | 102a,b |
| interconnection circuit board | 103 |
| velocity sensor coil (part of 105a,b) | 104a,b |
| board and keeper assembly (part of 100a,b) | 105a.b |
| torquer coil (part of 105a,b) | 106a,b |
| magnet keeper (part of 105a,b) | 108a,b |
| coil mounting board (part of 105a,b) | 109a,b |
| interface flange (part of 102a,b) | 110a,b |
| feed through terminals (part of 105a,b) | 116a,b,c,d |
| flexible leads | 118a,b,c,d |
| cable (part of 100a,b) | 120a |
| connector (part of 100a,b) | 122a,b |
| sensor assembly cap (part of 100a,b) | 124a.b |
| lateral stay | 130a,b |
| lateral stay | 132a,b |
| sensor assembly cable | 133 |
| cross arm | 136 |
| sensor assembly connector | 137 |
| torsion tube | 138 |
| key-slotted bushing | 139 |
| reaction torque sensor module | 140 |
| anchor plate | 141 |
| counterbored seat | 143a,b |
| key | 146a,b |
| circuit board | 147 |
| stand off terminal | 150a,b,c,d |
| washer | 152a,b |
| loading washer | 154a,b |
| self-locking adjustment nut | 156a,b,c,d |
| locking nut | 158a,b |
| stand off terminal | 159 a,b,c,d |
| bonded, polarized washer | 160a,b |
| insulating washer (part of 160a,b) | 162a,b |
| conductive tabbed washer (part of 160a,b) | 164a,b |
| polarized washer (part of 160a,b) | 165a,b |

-continued
PARTS LIST

| NOMENCLATURE | PART NO. |
| --- | --- |
| electrical lead | 166a,b,c,d |
| electromagnetic torquer | 180 |
| torque sensing circuit | 181 |
| torquer circuit | 182 |
| differential amplifier | 183 |
| operational standardization amplifier | 184 |
| operational standardization amplifier | 185 |
| magnetic circuit | 186 |
| summing resistor | 187 |
| summing resistor | 188 |
| power amplifier | 189 |
| angular velocity sensing circuit | 190 |
| adjustable gain isolation amplifier | 193 a,b |
| velocity sense detector | 194 |
| adjustable gain isolation amplifier | 195a,b |
| zero cross over detector | 196 |
| differential amplifier | 197 |
| power amplifier control logic circuit | 198 |
| density sensor wiring harness | 200 |
| density/gyroscopic mass flow sensor wiring harness | 202 |
| density/inferential mass flow sensor wiring harness | 204 |
| junction box | 210 |
| external system interface connector | 220 |
| signal conditioning circuit | 230 |
| signal conditioning circuit | 240 |
| signal format converter | 250 |
| signal format converter | 260 |
| volumetric flow sensor | 300 |
| signal conditioning circuit | 320 |
| signal format converter | 340 |
| differential pressure sensor | 350 |
| connector | 360 |

DESCRIPTION

INTRODUCTION

It is a characteristic of the sensor system herein described that the apparatus may be configured in different ways for different applications, while the general physical configuration, the dynamic operation, and the great majority of constituent parts and assemblies remain the same.

The detailed description of the preferred embodiment of the sensor of the invention, as given below, is based on an apparatus configuration suitable as a gyroscopic mass flow and density sensor for use with liquids. This embodiment is shown in FIG. 1.

Descriptions of other configurations suitable for the type of matter within or flowing through the sensor are also given in appropriate detail.

In the descriptions and discussions of the sensor of my invention contained in this patent application, certain terms are used in the sense that they are understood by the persons skilled in the art and science of engineering. To the best of my belief, the following definitions conform to contemporary engineering usage.

TO SEAL—to generally prevent the passage of matter (leakage) across a boundary.

IMPERMEABLE SEAL—any device that limits the passage of matter across a boundary to such a degree that such leakage is nominally zero for the application intended. (For example, a seal preventing the transfer of air into a food container might be impermeable in terms of that application. However, the same seal might very well be considered permeable for a gyro case containing helium.)

PERMEABLE SEAL—any device that limits the passage of matter across a boundary to a predetermined degree so that such leakage is tolerable for the application intended. (For example, a seal allowing transfer of air into or out of a shipping container, for the purpose of preventing over or under pressure within the container, would fit the definition above, but would be considered faulty if the seal also allowed the transfer of water.)

LABYRINTHINE SEAL—a special case of permeable seal where no physical element acts as a barrier to the flow of material across the seal. (For example, the bypass leakage of hot combustion gases through the case of a gas turbine is limited by controlling the clearance of the blade tips relative to the case. The limited passage area and the convoluted path through the casing form the laybrinthine seal.)

The field of electronic and electrical engineering has reached a stage of development where devices such as motors, amplifiers, filters, transducers, and many other devices which are quite complicated in their own right, are readily commercially available and considered conventional. Therefore, when high level descriptions of such relatively complex apparatus are required, it is normal engineering practice to refer to such devices as components and to represent them graphically by simple symbols, such as functional blocks with descriptive titles.

This convention has been followed in the text of this patent application and in the drawings herein.

The following list contains some of the conventional electrical and electronic elements so represented in the drawings:

| NOMENCLATURE | PART NO. |
| --- | --- |
| velocity sensor coil | 104 |
| torquer coil | 106 |
| bonded, polarized washer | 160 |
| differential amplifier | 183 |
| operational standardization amplifier | 184, 185 |
| power amplifier | 189 |
| adjustable gain isolation amplifier | 193, 195 |
| velocity sense detector | 194 |
| zero crossover detector | 196 |
| power amplifier control logic circuit | 198 |
| junction box | 210 |
| external system interface connector | 220 |
| signal conditioning circuits | 230, 240, 320 |
| signal format converters | 250, 260, 340 |
| volumetric flow sensor | 300 |
| differential pressure sensor | 350 |

MASS FLOW/DENSITY SENSOR-PREFERRED EMBODIMENT

FIG. 1 is an exploded, perspective view of the mass flow/density sensor. The view is taken looking down at the left side of the sensor.

A frame, vessel or housing 13 includes a perimetral member or base 15 which supports the remaining elements of the frame 13.

The perimetral member 15 is generally symmetric to a first reference plane x-y. The intersection of normal reference axes x and y is generally at the center of the perimetral member 15. A third reference axis, z, normal to the reference plane x-y, passes through the intersection point of axes x and y.

A housing, cone or support structure 30a extends from the left side of the perimetral member 15. Fasteners (34a, b, c, d) are provided to secure the assembly.

A cap or cover 40a is mounted on the end of housing 30a. Fasteners (44a,b,c,d) are provided to secure the assembly. The right side of the sensor is symmetric to the left side in this respect. A housing, cone or support structure 30b extends from the right side of the perimetral member 15.

A cap or cover 40b is mounted on the end of housing 30b. Fasteners (44e,f,g,h) are provided to secure the assembly.

Fluent traversing the perimetral member 15, of the sensor unit 1 passes through an internal conduit 50.

CONSTRUCTION OF INTERNAL CONDUIT 50

The internal conduit 50 includes a inertial reaction duct 52 between conduit extensions 55a,b and anchor collars 53a,b.

The flow path of the inertial reaction duct 52 is shaped so as to change direction relative to the flow axis as fluent traverses between extension conduit 55a and extension conduit 55b.

(For convenience of description and henceforth, flow is assumed in the direction of the x axis; however, the operation of the sensor is identical if the flow direction is reversed.)

An anchor collar 53a is fitted at the junction between conduit extension 55a and the inertial reaction duct 52. Symmetrically, anchor collar 53b is fitted at the junction between conduit extension 55b and the inertial reaction duct 52.

A cruciform bar 57 re-enforces the inertial reaction duct 52 so that the cruciform bar 57 and the internal reaction duct 52 form an integral unit with the internal conduit 50 between anchor collars 53a and 53b.

Flow is directed into the sensor from the port 20a via port extension 22a into the internal conduit 50 via the conduit extension 55a, which is substantially coaxial with port extension 22a.

An impermeable flexible seal 60a is fitted between port extension 22a and conduit extension 55a. This seal 60a is formed as a semi-toroid. One rim of the seal 60a is fixed to the port extension 22a, and the other rim is fixed to the conduit extension 55a so that a continuous barrier exists between the two elements. A similar seal 60b is installed between port extension 22b and conduit extension 55b.

RADIAL SUPPORT OF INTERNAL CONDUIT 50

The internal conduit 50 is radially positioned relative to the perimetral member 15 by four substantially equally spaced radial stays 90a, 90b, 91a and 91b. Each stay is threaded at each end. The mid plane of the internal conduit 50 is substantially in the x-y plane of perimetral member 15.

By design, the center of gravity of the internal conduit 50 is substantially at the intersection of the lines of action of said radial stay members 90a, 90b, 91a, and 91b. The conduit extensions 55a and 55b are positioned substantially along the reference axis x of the perimetral member 15.

The radial stays 90a, 90b, 91a and 91b are slender, elongated structural members of predetermined section modulus to length ratios, and predetermined section area to length ratios.

The radial stays 91a and 91b traverse clearance pass-throughs 99a and 99b in the inertial reaction duct 52. These pass-throughs 99a,b are large enough to insure that the inertial reaction duct 52 does not touch the stays 91a or 91b under any operating condition.

Radial stays 90a, 90b, 91a and 91b, are anchored at four anchor pads 92a,b,c,d on the perimetral member 15 and at four anchor pads 51a, 51b, 51c and 51d on the cruciform bar 57.

The anchor pad 92a is drilled and counterbored to allow passage of the outer threaded end of the radial stay 90a, which threaded end is engaged by a adjusting nut 95a. The pressure face of the adjusting nut 95a rests on a pair of self-aligning washers 93a and 94a, which rest on the face of anchor pad 92a. A locking nut 97a is fitted on the outer threaded end of radial stay 90a to engage the upper face of the adjusting nut 95a. These arrangements are typical of the locking and adjusting means at pads 92b,c and d on perimeteral member 15.

The inner threaded end of radial stay 90a engages a tapped hole in anchor pad 51a and a locking nut 97E is used to secure the joint. These arrangements are typical of the locking and adjusting means at anchor pads 51b,c and d.

A velocity sensor-torquer module 100a is installed in the perimetral member 15 of the sensor unit. FIG. 3 is a view of the velocity sensor-torquer assembly 100a exploded along the Y axis.

The velocity sensor-torquer assembly 100a includes housing 102a, board and keeper assembly 105a, sensor assembly cap 124a and connector 122a.

A key slot 11a in the perimeteral member 15 is used to orient the velocity sensor-torquer module 100a when it is installed in the perimetral member 15 utilizing the through bore 12a.

A mounting pad 14a, substantially square to the through bore 12a is provided on the perimetral member 15. Fasteners 46a,b,c and d are provided to secure the velocity sensor-torquer module 100a.

FIG. 4 is an exploded view of the board and keeper assembly, 105a.

Velocity sensor coil 104a and torquer coil 106a are mounted on coil mounting board 109a. The coil mounting board 109a is mounted on magnet keeper 108a. Interconnection circuit board 103a is secured atop magnet keeper 108a.

The leads from the velocity sensor coil 104a and from the coil torquer 106a are connected to feed through terminals 116a, b,c and d mounted on interconnection circuit board 103a. The feed through terminals 116a, b, c and d allow for attachment of cable 120a which is terminated in a connector 122a.

The connector 122a is mounted on the sensor assembly cap 124a which is mounted on the housing 102a.

Velocity sensor-torquer assembly 100b which is installed in the perimetral member 15 is of the same construction as velocity-sensor torquer assembly 100a and is installed in the same manner using key slot 11b, through bore 12b and fasteners 44f-h. Its location is substantially diametrically opposite and co-linear with velocity sensor-torquer assembly 100a.

Interconnections between the electrical elements included in a velocity sensor-torquer assemblies 100a and 100b are accomplished in the wiring harness 202 and in the junction box 210. (See FIG. 10d.)

LATERAL SUPPORT OF INTERNAL CONDUIT 50

The internal conduit 50 is restrained along the z axis of the mass flow/density sensor by lateral stays 130a and 130b and lateral stays 132a and 132b.

The lateral stays 130a and 130b and the lateral stays 132a and 132b are slender elongated structural members of predetermined section modulus to length ratios, and predetermined section area to length ratios.

The lateral stays 130a and 130b lie generally in the yz plane of the sensor and are generally symmetric to the z axis of the sensor.

The lateral stays 132a and 132b lie generally in the xz plane of the sensor, and are generally symmetric to the z axis of the sensor.

At the left end of the sensor, the lateral stays 130a and 130b are anchored on cross arm 136 of torsion tube 138. The cross arm 136 is integral with the torsion tube 138.

The torsion tube 138 seats in a slot in keyslotted bushing 139 and is secured by the lateral stays 130a and 130b.

The key-slotted bushing 139 is mounted on housing 30a. Orientation is maintained by means of key 146a in between housing 30a and key-slotted bushing 139.

One threaded end of lateral stay 130a passes through a clearance opening in the cross arm 136 and through washer 152a. The threaded end of the lateral stay 130a is engaged by self-locking adjustment nut 156a.

The other threaded end of lateral stay 130a engages a threaded hole in the cruciform bar 57, after passing through a clearance opening in permanent bar magnet 70a. Locking nut 71a stabilizes the joint.

One threaded end of the lateral stay 130b passes through a clearance opening in the cross arm 136 and through a washer 152b. The threaded end of the lateral stay 130b is engaged by the self-locking adjustment nut 156b.

The other threaded end of the lateral stay 130b engages a threaded hole in the cruciform bar 57 after passing through a clearance opening in the permanent bar magnet 70b. Locking nut 71b stabilizes the joint.

At the right end of the sensor unit the lateral stays 132a and 132b are anchored on anchor plate 141 which is part of reaction torque sensor module 140. The plate 141 is mounted on the housing 30b.

The lateral stay 132a passes through a washer stack comprising the following elements: bonded, polarized washer 160a and loading washer 154a. The threaded end of the lateral stay 130a is engaged by the self-locking adjustment nut 156a.

The lateral stay 132b passes through a washer stack comprising the following elements: bonded, polarized washer 160b and loading washer 154b. The threaded end of the lateral stay 130b is engaged by the self-locking adjustment nut 156b.

The other threaded end of lateral stay, 132a engages a tapped hole in the anchor collar 53a. Locking nut 158a secures the joint.

The other threaded end of lateral stay, 132b engages a tapped hole in the anchor collar 53b. Locking nut 158b secures the joint.

The radial and lateral stay system is adjusted so that all stays are in tension and the internal conduit 50 is generally centered relative to the frame 13.

FIG. 5 is a view of the reaction torque sensor assembly 140. The view is taken from the right end of the sensor unit as shown in FIG. 1.

The input and output leads from the electrical elements are formed into a sensor assembly cable 133 which is led into the junction box 210 via sensor assembly connector 137.

FIG. 6 is an exploded view along the z axis of bonded, polarized washer 160a, which comprises insulating washer, 162a; conductive tabbed washer 164a; polarized washer 165a; conductive tabbed washer 164b and insulating washer 162b. Electrical lead 166a is connected to conductive tabbed washer 164a, and electrical lead 166b is connected to conductive tabbed washer 164b.

The anchor plate 141 is provided with stand off terminals 150a, b, c and d to which electrically conductive leads from the bonded, polarized washer 160a and from the bonded, polarized washer 160b are connected.

The bonded, polarized washers 160a,b are included in the torque sensing circuit 181 (see FIG. 8) whose elements are mounted on circuit board 147, which in turn is mounted on the anchor plate 141. The electrical elements of circuit 181 include: bonded, polarized washers 160a,b; adjustable gain isolation amplifiers 193a and 193b; summing resistor 187; differential amplifier 183a; and operational standardization amplifier 184. The interconnections for circuit 181 are shown in the block diagram in FIG. 8. Circuit 181 also rejects the common modes of the signals originating in washers 160a and b.

(Adjustable gain isolation amplifiers 193a and b are respectively driven by bonded, polarized washers 160a and b. These amplifiers are adjusted during manufacture to equalize the force-to-signal characteristics of the individual washers, 160a and b.)

The signals from the amplifiers, 193a and b are applied to the summing resistor 187. The signal across the summing resistor 187 is applied to the differential amplifier 183, and thence to operational standardization amplifier 184. The output of operational standardization amplifier 184 is transmitted to the signal conditioning circuit 240 and thence to the signal format converter 260 which is a variable, application-specific circuit that is configured to meet the specification of the end user of the sensor. The signal format converter, 260 is the interface with the external system (See FIG. 10A).

The conventional elements in these circuits are represented by labeled blocks which identify the function performed by each element.

VELOCITY SENSOR AND TORQUER ASSEMBLY

FIG. 9 is a perspective view of the permeable elements of magnetic circuit 186, with generally symmetric air gaps 68a,b,c and d, and includes permanent bar magnet 70a; and magnet keeper 108a. Permanent bar magnet 70b and magnet keeper 108b are cyclic elements in the magnetic circuit 186.

FIG. 7A is a diagram of angular velocity sensing circuit 190. The circuit includes a summing resistor 188 which is in series with velocity sensor coil 104a and b. The outputs of coils 104a,b are respectively fed into adjustable gain isolation amplifiers 193a,b. These adjustable gain isolation amplifiers 193a,b are adjusted at manufacture to equalize the velocity-to-signal characteristics of each individual coil 104a,b. The voltage drop across the summing resistor 188 is applied to the differential amplifier 197. The signal from the differential amplifier 197 is sent to the operational standardization amplifier 185. The signal from the operational standardization amplifier 185 is transmitted to the signal conditioning circuit 230 which is mounted in the junction box 210. The circuit connections are accomplished via the wiring harness 200.

The signal conditioning circuit 230 feeds a signal format converter 250 which is a variable, application-specific circuit which is configured to meet the specification of the end used of the sensor. The signal format converter 260 is the interface with the external system.

The conventional elements in these circuits are represented by labeled blocks which identify the function performed by each element.

The plan form of each velocity sensor coil 104a and b is generally rectangular and the plane of each coil 104a and b is generally oriented normal to the lines of flux in the magnetic circuit air gaps 68a,b,c and d. The longer leg of each coil 104a and b lies generally above a pole of the permanent bar magnets 70a and 70b and runs generally parallel to the x axis of the sensor.

FIG. 7B is a functional block diagram of the torquer circuit 182. The circuit, which receives an input from the angular velocity sensing circuit 190, includes a velocity sense detector, 194, a zero crossover detector 196, a power amplifier control logic 198 and a power amplifier 189 which energizes electromagnetic torquer coils 106a and b which are connected in series. The torquer coils 106a and b are formed as solenoids of generally rectangular plan form. Circuit interconnections are accomplished via the wiring harness 200. The power amplifier 189 is mounted in the junction box 210.

THEORY AND OPERATION OF THE MASS FLOW/DENSITY SENSOR

The theory and the operation of the mass density sensor used in any of the various configurations of the sensor of my invention is the same for any useful combination of sensor constituent elements chosen for a given application.

In application, the sensor is installed in an external system conduit.

The sensor receives suitable power and control signals from the external system. The sensor has two states: "OFF" and "TRANSMIT" which are controlled by the external system. In the "OFF" state, the sensor is de-energized. In the "TRANSMIT" state, the internal conduit drive and angular motion pick up systems are energized and the internal conduit oscillates relative to the frame at the natural frequency of the internal conduit-connecting stay system, and all electronics are activated.

In all configurations, the sensor transmits signals to the external system representing the instantaneous angular velocity of the internal conduit relative to the frame.

When the sensor has been configured for use in an inferential mass flow metering system (see FIGS. 2A and 2B), the system also transmits to the external system signals representing the instantaneous volumetric flow rate of the fluent traversing the sensor.

When the sensor has been configured for use in a gyroscopic mass flow metering system (see FIGS. 1, 2 and 2c), the sensor also transmits to the external system signals representing the instantaneous gyroscopic reaction torque that the internal conduit exerts on the frame.

THEORY OF OPERATION IN THE DENSITY SENSOR CONFIGURATION

The natural frequency of oscillation of an idealized single degree of freedom, second order spring-mass torsional mechanical oscillator with a constant linear spring is a function of the mass moment of inertia of the mass element for any given geometric configuration of the system.

It follows that if the geometry of the system is known and is kept constant, the value of the mass moment of inertia may be computed from knowledge of the natural frequency of the oscillating system.

Further, if the mass is in the form of the mass of the internal conduit of a density meter plus the mass of the matter within the internal conduit, and the mass moment of inertia of the empty internal conduit is known, the density of the matter within the internal conduit may be computed.

It will be recognized that in a practical instrument, the idealizations of the above description can only be approximated. However, with careful design a useful degree of approximation to the ideal can be achieved for engineering applications.

THEORY OF OPERATION IN THE INFERENTIAL MASS FLOW SENSOR CONFIGURATION

If the mass density of a fluent and its volumetric flow rate are known, then the mass rate of flow can be computed.

When dealing with compressible fluents, it is necessary to assure that the determinations of both the mass density of the fluent and the volumetric rate of flow of the fluent be carried out with the fluent at the same state of pressure and temperature for both determinations. While absolute simultaneity of measurement is not possible, careful design of a practical instrument can achieve a very close approximation to the ideal case.

THEORY OF OPERATION OF THE GYROSCOPIC MASS FLOW SENSOR

The basic principle of operation of both gyroscopic and coriolis mass flow sensors derive from Newton's principle that a force is required to change the momentum of mass particle. This principle is stated in terms of both the angular and linear momentum of the mass particle.

Since either angular or linear momentum is a vector quantity, a change in momentum may be caused by changing either the magnitude or the direction of its vector.

A mass particle constrained to flow within a duct possesses momentum due to its motion. If the direction of flow of the particle between two sections of the duct changes, at least part of the momentum of the particle can be expressed in terms of its angular momentum as its direction changes. The net angular momentum of the matter contained between the two sections can be expressed as the integral of the angular momentum of each of the particles within the duct. This angular momentum is a function of the mass rate of flow of the matter and the equivalent radius of gyration of the duct between the two sections.

When matter is flowing within the duct, any angular rotation of the duct, continuous or oscillatory, which changes the direction of the net angular momentum vector will cause inertial reactions to be imposed on the duct.

Note that the above discussion is general in nature and given the single condition that "the direction of flow of the particle between two sections of the duct changes" is independent of the size, shape or radius of gyration of the duct and the state (liquid, gaseous or multiphasic slurry) of the matter. The change of direction may take a meandering, curved, circuitous or polygonal flow path without invalidating the argument.

This principle of operation is expressed both in the coriolis equation $$F_x = 2MV_z X \omega_y \qquad (1)$$

Where
$F_x$ = Force
$MV_z$ = Linear Momentum of Reference Mass
$\omega_y$ = Angular velocity of Reference axes (for the sensor, of the internal conduit 50)
and X indicates the vector cross product
and in the gyroscopic equation $$T_x = H_z X \omega_y \qquad (2)$$

Where
$T_x$ = Torque
$H_z$ = Angular momentum of rotating reference mass
$\omega_y$ = Angular velocity of precession of the rotating reference mass (for the sensor, of the internal conduit 50)
and X indicates the vector cross product.

In both equations, all quantities are vectors referred to axes of orthogonal inertial reference frames as indicated by subscripts.

It is my belief that the fundamental design principle of the sensor of my invention, described herein, is best expressed by Equation 2 above, and that, while an alternative analysis based on Equation 1 above could be made with equal rigor, the gyroscopic form is more convenient.

By suitable algebraic substitution in Equation 2 above, the angular momentum of the matter in the duct can be related to the mass flow rate.

In particular (reference Equation 2 above), if we know the angular velocity of the duct at any instant and the torque exerted on the duct by the fluent matter due to the inertial reaction to that angular velocity, we may compute the angular momentum of the matter, and, from knowledge of the physical constants of the sensor, compute the value of the mass flow rate of the matter.

The mass flow/mass density sensor of the invention, in each of its configurations utilizes as mechanical "building blocks":
a) a single degree of freedom, second order mechanical torsion oscillator
b) a generally "string supported" inertial reaction conduit internal to the sensor unit.
c) specialized seals between the sensor unit entry ports and the internal conduit so that the sensor elements and materials of construction can be economically adapted to various types of service.

We will review the theory of these elements of construction as they are understood in the context of this specification.

THEORY OF SINGLE DEGREE OF FREEDOM, SECOND ORDER MECHANICAL OSCILLATORS

It is proved in standard texts on mechanical vibrations (e.g., Mechanical Vibrations, J. P. den Hartog, Chapter 2, Third Edition) that the motions of an idealized, undamped, single degree of freedom oscillator can be very closely approximated by the motions of a lightly damped, spring-mass physical system so constructed that the inertial mass element and the spring element can be treated as lumped constants, and that the base of the system and the inertial mass can each be treated as a rigid element.

It is further shown that if such physical systems are perturbed by an impulsive input (motion, torque or force), they will oscillate at a natural frequency very close to the natural frequency of an idealized, undamped system with the same nominal physical characteristics, and that a displacement versus time history of such motion will very closely approximate a cosine wave.

It is further shown that if the energy lost to damping in such physical systems is cyclically replaced, such physical systems will continue to oscillate at a natural frequency very close to the natural frequency of an idealized undamped system with the same nominal physical characteristics, and that a displacement versus time history of such motion will very closely approximate a cosine wave. From a further consideration of Raleigh's method (section 32 et seq)(J. P. den Hartog, op cit) it will be seen that stable cyclic oscillatory motion can exist for many nonlinear systems. Thus, while approximate linearity is desirable for many applications, it is not strictly necessary for the operation of the sensor.

THEORY OF STRING-SUPPORTED BODIES

A string is defined as an elongated structural member that can support only tension loads.

If a body is supported relative to a reference frame by a set of strings, the resultant external forces acting on the body can be determined by vectorial summation of the tension forces being exerted by the set of strings. In addition, the resultant external torque acting on the body can be determined by computing the sum of the vectorial products of the tension forces exerted by each of the strings in the set multiplied by the moment arm (distance) from the axis of each string to a reference axis or point.

With careful practical design, physical stays with predetermined length to section modulus ratios and predetermined length to section area ratios can approximate a theoretical ideal string to a degree of accuracy sufficient for the application intended. The stay section modulus and the stay area are measured transverse to the longitudinal axis of the stay.

In the practical design of a stay-supported body, it may be desirable to connect the body to a frame by auxiliary members such as ducts, signal and/or power leads or other devices. These members will have some capability for structural support of the body. With careful design, the compliance of these members can be made much greater than the compliance of the string set.

When the design conditions referred to above are observed, the behavior of such a stay-supported body will approximate that of a purely string-supported body to a degree of accuracy sufficient for the application intended.

THEORY OF LABYRINTHINE SEALS

A labyrinthine "seal" for matter is defined as high resistance leakage passage through which the matter being "sealed" may pass, at a rate which may be tolerated for the application for which the seal is intended.

It is the usual condition for a practical flow sensor that all flow that enters the sensor is accounted for by the calibration constant of the sensor. In a practical instrument any fraction of flow allowed to bypass the sensitive element of the sensor must be very small and/or the value of the fraction must be nearly constant over the rated flow range and pressure range of the sensor.

These conditions are met if the labyrinthine seal flow channel has a small net flow area, relative to the main flow duct, and the Reynolds numbers for the labyrinthine seal flow channel and the main flow duct are nearly equal. In many practical cases, the behavior of the labyrinthine seal can be acceptably approximated by a permeable seal of more conventional type. The permeability may be controlled by the porosity of the seal material or by by-pass orifices.

OPERATION OF THE MASS DENSITY AND MASS FLOW SENSOR IN THE GYROSCOPIC MODE

Refer to FIG. 1 which is an exploded view of the mass flow/density sensor configured for the flow of liquids, gases or slurries traversing the internal conduit 50 in either direction.

Flow enters the internal conduit 50 via the conduit extension 55a which is substantially co-axial with and extends into port extension 22a.

Flow through the internal conduit 50 is discharged from the internal conduit 50 through conduit extension 55b and the port extension 22b.

Leakage of matter during the transfer from the port extension 22a into the internal conduit 50 via the conduit extension 55a is prevented by an impermeable flexible seal 60a. Similarly, leakage of matter during the transfer into the port extension 22b from the internal conduit 50 via the conduit extension 55a is prevented by an impermeable flexible seal 60b.

When the sensor is configured for the flow of matter in the form of gases or vapors, and permeable or labyrinthine seals are used, the frame 13 is sealed using sealing element 17 so that frame 13 forms an impermeable vessel.

The operation of the sensor as given in this patent application is the same for any of the configurations and modes of operation of the sensor, except that for the density determination-only configuration and the inferential mass flow sensor configurations, the torque reaction sensor module 140 is not used.

FUNCTIONAL ASPECTS OF THE CONSTRUCTION OF THE SENSOR

As indicated in FIG. 1, the conduit, sensor flow, 50 is connected to the frame 13 by a set of Two radial stays 90a and 90b
Two radial stays 91a and 91b
Two lateral stays 130a and 130b
Two lateral stays 132a and 132b Each of these stays has the functional characteristics of a string in tension. The line of action of each of the four radial stays 90a,b and 91a,b passes substantially through a common point, which by design is very nearly at the center of gravity of the internal conduit 50. Theore, these elements can exert only a very small torque on the internal conduit 50.

Conversely, since there are moment arms between the two lateral stays, 130a and 130b and the two lateral stays 132a and 132b, these elements can exert torques on the internal conduit 50. Since the moment arms of each of these lateral pairs of stays are very nearly in quadrature which each other, torques about the x axis are effectively isolated from torques about the y axis.

The design of the sensor is such that the assembled frame 13 is relatively massive and rigid, and the internal conduit 50 acts as a practically rigid, lumped inertial element. These design features prevent undesirable interactions between vibratory modes of the sensor.

In this discussion, we have neglected the masses and compliances associated with the other structural elements (stays, washers, torsion arms, etc.) between the internal conduit 50 and the frame 13. As previously indicated (see Theory of String-supported Bodies, above), with careful design, these masses may be kept so small and compliances may be kept so large and constant that they do not effect the practical performance dynamics of the sensor.

DYNAMICAL OPERATION OF THE SENSOR

When the sensor is in the "TRANSMIT" state, the electromagnetic torquer 180 is energized and causes the internal conduit 50 to oscillate around the flow axis x.

The angular velocity sensing circuit 190 detects the motion of the internal conduit 50 around the x axis, and generates signals representative of such motion which are transmitted to the external system and to the electromagnetic torquer 180.

The torque sensing circuit 181 detects oscillatory torque reactions around the torque reaction axis y exerted by the internal conduit 50 on the frame 13, and generates signals representative of such torque. These signals are transmitted to the external system.

OPERATION OF THE ELECTROMAGNETIC TORQUER 180

The electromagnetic torquer 180 includes the torquer circuit 182 (see FIG. 7b) and the magnetic circuit 186 (see FIG. 9), and is activated when the sensor is in the "TRANSMIT" state. The electromagnetic torquer 180 is analogous to a conventional electric motor.

When current is passed through the torquer circuit 182, magnetic poles are formed by the torquer coils 106a and b which attract magnetic poles of opposite sense on the permanent bar magnets 70a and b. The sense of the current in each of the torquer coils 106a,b is such that the attraction caused by the magnetic poles acts in an additive manner to produce torque on the internal conduit 50.

The torque exerted on the internal conduit 50 is controlled by the torquer circuit 182 shown in FIG. 7B, the block diagram of this circuit.

As shown in FIG. 7B, signals from the angular velocity sensing circuit 190 are transmitted (inputted) to the velocity sense detector 194 and to the zero crossover detector 196. The output signals from these detectors are transmitted to the power amplifier control logic circuit 198.

The logic elements in the power amplifier control logic circuit 198 are so arranged as to produce a predetermined energizing signal as a function of the state of the input signals from the velocity sense detector 194 and the zero crossover detector 196. The energizing signal is inputted to the power amplifier 189 which, in turn, pulses the torquer coils 106a and b at predetermined times during the oscillation of the internal conduit 50. The torque thereby created excites and maintains the oscillation of the internal conduit 50.

OPERATION OF THE ANGULAR VELOCITY SENSING CIRCUIT 190

The angular velocity sensing circuit 190 includes the velocity sensor coils 104a,b (see FIG. 7A) and the magnetic circuit 186 (see FIG. 9).

When the internal conduit 50 oscillates about the x axis, the magnetic flux in the air gaps 68a,b,c,d in the magnetic circuit 186 moves transversely relative to the velocity sensor coils 104a and 104b in the angular velocity sensing circuit 190.

This motion induces a voltage proportional to the instantaneous angular velocity of the oscillation of the internal conduit 50 in the velocity sensor coils 104a and b. The value of these voltages are a representation of the angular velocity of precession $\omega_y$ of the material flowing in internal conduit 50. (See equation 2 previously presented in the section headed "Theory of Operation of the Gyroscopic Mass Flow Sensor".)

The voltages produced in velocity sensor coils 104a and b are applied across the summing resistor 188 which is of predetermined value. This voltage is applied to the input of an differential amplifier 197 whose output voltage is applied to the input of operational standardization amplifier 185, whose output is the signal source for transmission to the host system. The gain of the operational standardization amplifier 185 is adjusted to standardize the calibration of the angular velocity sensing circuit 190.

The output of the operational standardization amplifier 185 is fed into signal conditioning circuit 230 which may have application-dependent characteristics such as peak detection, analog-to-digital conversion or voltage-to-optical conversion features to suit the interface requirements of the external system.

OPERATION OF THE TORQUE REACTION SENSOR

When there is flow through the sensor and the internal conduit 50 is in oscillatory motion relative to the frame 13 about the x axis, the fluent exerts a gyroscopic torque reaction about the y axis. (See equation 2 previously presented in the section headed "Theory of Operation of the Gyroscopic Mass Flow Sensor".)

This reaction torque is balanced by forces exerted by the lateral stays 132a,b which act across their known and equal moment arms. The forces exerted by the lateral stays 132a,b are transmitted through the bonded, polarized washers 160a,b, to frame 13.

The bonded, polarized washers 160a,b are piezo-electric sensitive elements, and the forces cause electrical voltages to be generated in the torque sensing circuit 181. (See FIG. 8)

The voltage produced in bonded, polarized washers 160a,b are each applied to adjustable gain isolation amplifiers 193a and b, respectively, whose gains are set so that the force-to-voltage ratios from both washer-amplifier combinations match arbitrarily closely.

The outputs of amplifiers 193a and b are connected across the summing resistor 187 which is of predetermined value. This voltage is applied to the input of an differential amplifier 183, whose output is fed to operational standardization amplifier 184 whose gain is adjusted to standardize the calibration of the torque sensing circuit 181. The output of the operational standardization amplifier 184 is fed into signal conditioning circuit 240 which may have application-dependent characteristics such as peak detection, analog-to-digital conversion or voltage-to-optical conversion features to suit the interface requirements of the external system.

See the section of this application that deals with the theory of operation of the gyroscopic mass flow sensor for an explanation of how the signals from the sensor may be processed by the external system to determine the mass flow rate through the sensor.

OPERATION OF THE SENSOR IN THE MASS DENSITY DETERMINATION MODE

The operation of the sensor when configured in the mass density mode is the same as when it is configured as a mass density/rate of flow sensor as described above, except that the torque sensing circuit 182 is not used. (See FIG. 10B.)

See the section of this application that deals with the theory of operation of the mass density sensor for an explanation of how the signals from the sensor may be processed by the external system to determine the density of matter inside or flowing through the sensor.

OPERATION OF THE SENSOR IN THE MASS DENSITY/INFERENTIAL MASS FLOW RATE DETERMINATION MODE

The operation of the sensor when configured in the mass density/inferential mass flow rate mode is the same as when it is configured as a mass density/rate of flow sensor as described for the gyroscopic mass flow sensor, except that the torque sensing circuit 182 is replaced by the integral fluent velocity sensor or the volumetric flow sensor 300. Further, the signal conditioning circuit 320 and the signal format converter 340 replace the signal conditioning circuit 240 and the signal format converter 260 (See FIG. 10c.). The functions of the corresponding circuits remain the same.

OPERATION OF THE VOLUMETRIC FLOW SENSOR

In FIGS. 2a and 2b the volumetric flow sensor 300 embodiment is shown schematically as a venturi tube connected to a differential pressure sensor, whereby the pressure drop between the venturi throat and the pressure in the approach section can be measured. This system of fluent volumetric measurement is very well known and needs no further explication.

See the section of this application that deals with the theory of operation of the inferential mass density/mass flow sensor for an explanation of how the signals from the sensor may be processed by the external system to determine the density and mass flow rate through the sensor.

CONCLUSIONS, RAMIFICATIONS AND SCOPE OF INVENTION

The mass flow/density sensor of the invention provides an accurate, reliable, long-lived, highly cost-effective sensor that can be used in a wide variety of applications where it is desired to measure the density and/or the mass flow rate of matter moving within a conduit.

While the above description contains many specific details of construction, these should not be construed as limitations on the scope of the invention but rather as examples of the preferred embodiments of the invention. Many other variations are possible. For example:

The number and the arrangement of the stays generally supporting the internal conduit may be varied, as may the number and arrangement of the internal conduit torquer, the internal conduit angular velocity motion sensors and the internal conduit torque reaction transducer devices. The form of the particular ramifications will be evident to those skilled in the art and theory of string supported bodies, velocity/motion sensors, torque/force reaction transducers, and electro-mechanical torquer and motor devices.

The stays may be in the form of properly oriented tapes, wire rope cables or composite fiber bundles of constant or variable cross section.

Capacitive, optical or fluid amplifier means may be used to determine the angular velocity of the internal conduit 50 relative to the frame 13.

Capacitive, gas impingement or direct contact means may be used to exert torque on the internal conduit 50 relative to the frame 13.

The internal conduit 50 and its connecting system may be driven to oscillate at some arbitrary frequency instead of its natural frequency and the density of the matter may be computed from the power requirement of the drive.

The significant torsional elastic restraint member or members (about the x axis) of the internal conduit 50 may be configured as helical springs, disc springs or other conventional mechanical elastic elements.

The torquer circuit 182 may use bending piezo-electric elements, piezo-resistive elements, or capacitive elements.

The permeable flexible seal 62 may be fabricated from a closed cell foamed elastomer.

The labyrinthine seal may be approximated by an open cell foamed elastomer sleeve filling in the annulus between the conduit extension 55a which is substantially co-axial with port extension 22a and extends into the port extension 22a.

The mechanical design technique, known as kinematic or structural inversion to those skilled in the art, may be used to interchange the various elements of the invention. For example, the internal conduit 50 may be connected to the frame by an internal support member, rather than by a perimetral member.

Accordingly, the scope of the invention should be determined not by the embodiment(s) illustrated, but by the appended claims and their legal equivalents.

I claim:

1. An apparatus for measuring mass density of matter including:
a) a frame having a plurality of interface ports, wherethrough matter can enter and exit, and three mutually orthogonal axes, respectively designated x, y, and z, said axes having a common predetermined origin;
b) at least one conduit with ends respectively positioned in said interface ports:
c) a plurality of stays coupled to said frame and said at least one conduit to secure said at least one conduit to said frame, each stay having a length, width, area, and cross section transverse to said length, each cross section having a predetermined ratio of section modulus to length and a predetermined ratio of cross section area to length, such that each stay has a structural compliance characteristic equivalent to that of a string;
d) motor means coupled to said conduit for exerting a torque thereon; and
e) motion transducer means coupled to said conduit for detecting angular motion of said conduit around at least one of said axes.

2. The apparatus of claim 1 further including:
a) a torquer and angular motion detector coupled to said conduit, said torquer and angular motion detector having a common magnetic circuit, said magnetic circuit having a plurality of air gaps;
b) generating means magnetically coupled to said conduit and having a plurality of electrically conducting coils electrically coupled to said common magnetic circuit, and permanent or electromagnetic means for creating magnetic flux in air gaps of said magnetic circuit;
c) electrical circuit means coupled to said generating means for detecting electrical signals in at least one coil of said plurality of electrically conducting coils;
d) at least one other coil of said plurality of electrically conducting coils positioned relative to at least one air gap to a magnetic pole of predetermined polarity when electrical current flows through said at least one other coil, said magnetic pole creating a magnetic reaction force in said generating means;
e) electrical circuit means coupled to said generating means for controlling amplitude, direction, and duration of electrical current flow in said at least one other coil.

3. The apparatus of claim 1 wherein:
a) at least one stay of said plurality of stays is positioned in a plane parallel to a plane containing said x and y axes;
b) at least one other stay of said plurality of stays is positioned in a plane parallel to a plane containing said y and z axes, said at lest one other stay being parallel to said z axis.

4. An apparatus for measuring mass density of matter including:
a) a frame having a plurality of interface ports, wherethrough matter can enter and exit, at least two interface ports having linear extensions with a predetermined length-to-cross section area ratio, and three mutually orthogonal axes, respectively designated x, y, and z, said axes having a common predetermined origin, said linear extension positioned on said x axis;
b) at least one conduit, having linear end sections extending from said meandering path along said x axis;
c) means for coupling said linear end sections to said interface ports of said frame in a manner to limit leakage of said matter to be equal to or less than a predetermined fraction of a flow rate of said matter;
d) a plurality of stays coupled to said frame and said at least one conduit to secure said at least one conduit to said frame, each stay having a length, width, area, and cross section transverses to said length, each cross section having a predetermined ratio of section modulus to length and a predetermined ratio of cross section area to length, such that each stay has a structural compliance characteristic equivalent to that of a string;
e) motor means coupled to said conduit for exerting a torque thereon; and
f) motion transducer means coupled to said conduit for detecting angular motion of said conduit around at least one of said axes.

5. The apparatus of claim 4 further including:
a) a torquer and angular motion detector coupled to said conduit, said torquer and angular motion detector having a common magnetic circuit, said magnetic circuit having a plurality of air gaps;

b) generating means coupled to said conduit and having a plurality of electrically conducting coils coupled to said common magnetic circuit for creating magnetic flux in air gaps of said magnetic circuit;

c) electrical circuit means coupled to said generating means for detecting electrical signals in at least one coil of said plurality of electrically conducting coils;

d) at least one other coil of said plurality of electrically conducting coils positioned relative to at least one air gap to establish a magnetic pole of predetermined polarity when electrical current flows through said at least one other coil, said magnetic pole creating a magnetic reaction force in said generating means;

e) amplitude means coupled to said generating means for controlling amplitude, direction, and duration of electrical current flow in said at least one other coil.

6. An apparatus in accordance with claim 5 wherein said torquer comprises:

a) motion transducer means having at least one pair of electrically conductive coils coupled to said frame;

b) electrical circuit means coupled to said at least one pair of electrically conductive coils for subtractively combining signals from said at least one pair of electrically conductive coils to cancel common mode signals.

7. The apparatus of claim 4 wherein:

a) at least one stay of said plurality of stays is positioned in a plane parallel to a plane containing said x and y axes;

b) at least one other stay of said plurality of stays is positioned in a plane parallel to a plane containing said y and z said at least one other stay being parallel to said z axis.

8. The apparatus of claim 4 wherein a) said coupling means includes leakage limiters constructed of flexible material positioned between said linear end sections of said at least one conduit and said at least two interface ports.

9. The apparatus of claim 8 wherein a) said leakage limiter comprises a semi-toroid formed by dividing a toroid into two symmetrical halves through a plane normal to a polar axis of said toroid.

10. The apparatus of claim 4 wherein a) at least one linear extension of said at least one conduit and a corresponding interface port are concentric and further including at least one labyrinthine leakage limiter positioned between said at least one linear extension and said corresponding interface port.

11. The apparatus of claim 4 further including a) at least one elastic conduit constructed to have a compliance relative to said frame that is greater than that of said plurality of stays relative to said frame.

12. An apparatus for measuring mass flow rate of matter comprising:

a) a frame having a plurality of interface ports, wherethrough matter can enter and exist, at least two interface ports having linear extensions with a predetermined length-to-cross section area ratio, and three mutually orthogonal axes, respectively designated x, y, and z, said axes having a common predetermined origin, said linear extension positioned on said x axis;

b) at least one conduit, having a meandering path and linear end sections extending from said meandering path along said x axis;

c) means for coupling said linear end sections to said interface ports of said frame in a manner to limit leakage of said matter to be equal to or less than a predetermined fraction of a flow rate of said matter;

d) a plurality of stays coupled to said frame and said at least one conduit to secure said at least one conduit to said frame, each stay having length, width, area, and cross section transverse to said length, each cross section having a predetermined ratio of section modulus to length and a predetermined ratio of cross section area to length, such that each stay has a structural compliance characteristic equivalent to that of a string;

e) motor means coupled to said conduit for exerting a torque thereon;

f) motion transducer means coupled to said conduit for detecting angular motion of said conduit around at least one of said axes, and g) force transducer means coupled to said stays for detecting a level of force exerted on at least one of said stays.

13. The apparatus of claim 12 further including:

a) a torquer and angular motion detector coupled to said conduit, said torquer and angular motion detector having a common magnetic circuit, said magnetic circuit having a plurality of air gaps;

b) generating means coupled to said conduit and having a plurality of electrically conducting coils coupled to said common magnetic circuit for creating magnetic flux in air gaps of said magnetic circuit;

c) electrical circuit means coupled to said generating means for detecting electrical signals in at least one coil of said plurality of electrically conducting coils;

d) at least one other coil of said plurality of electrically conducting coils positioned relative to at least one coil of said plurality of electrically conducting coils;

d) at least one other coil of said plurality of electrically conducting coils positioned relative to at least one air gap to establish a magnetic pole of predetermined polarity when electrical current flows through said at least one other coil, said magnetic pole creating a magnetic reaction force in said generating means;

e) electrical circuit means coupled to said generating means for controlling amplitude, direction, and duration of electrical current flow in said at least one other coil.

14. An apparatus in accordance with claim 13 wherein said torquer and angular motion detector comprises:

a) motion transducer means having at least one pair of electrically conductive coils coupled to said frame;

b) electrical circuit means coupled to said at least one pair of electrically conductive coils for subtractively combining signals from said at least one pair of electrically conductive coils to cancel common mode signals.

15. The apparatus of claim 12 wherein:

a) at least one stay of said plurality of stays is positioned in a plane parallel to a plane containing said x and y axes;

b) at least one other stay of said plurality of stays is positioned in a plane parallel to a plane containing said y and z axes, said at least one other stay being parallel to said z axis.

16. The apparatus of claim 12 wherein
a) said coupling means includes leakage limiters constructed of flexible material positioned between said linear end sections of said at least one conduit and said at least two interface ports.

17. The apparatus of claim 16 wherein
a) said leakage limiter comprises a semi-toroid formed by dividing a toroid into two symmetrical halves through a pane normal to a polar axis of said toroid.

18. The apparatus of claim 12 wherein
a) at least one linear extension of said at least one conduit and a corresponding interface port are concentric and further including at least one labyrinthine leakage limiter positioned between said at least one linear extension and said corresponding interface port.

19. The apparatus of claim 12 further including at least one elastic conduit constructed to have a compliance relative to said frame that is greater than the compliance of said plurality of stays relative to said frame.

20. The apparatus of claim 12 wherein:
a) said force transducer means are coupled to at least two of said stays, said at least two of said stays being in a plane containing said x and z axes to provide at least two signals respectively representative of force applied to each of said at least two stays; and wherein said apparatus further includes
b) electric circuit means coupled to receive said at least two signals for subtractively combining said at least two signals in a manner that cancels common mode signals.

* * * * *